US010311210B2

(12) United States Patent
Grady et al.

(10) Patent No.: US 10,311,210 B2
(45) Date of Patent: *Jun. 4, 2019

(54) SYSTEMS AND METHODS FOR PROVIDING AN INDUCEMENT OF A PURCHASE IN CONJUNCTION WITH A PRESCRIPTION

(71) Applicant: LDM Group, LLC, St. Louis, MO (US)

(72) Inventors: James Grady, St. Louis, MO (US); David Christenson, St. Louis, MO (US); Robert Uecker, Cincinnati, OH (US)

(73) Assignee: LDM Group, LLC, St. Louis, MO (US)

( * ) Notice: Subject to any disclaimer, the term of this patent is extended or adjusted under 35 U.S.C. 154(b) by 335 days.

This patent is subject to a terminal disclaimer.

(21) Appl. No.: 14/296,098

(22) Filed: Jun. 4, 2014

(65) Prior Publication Data
US 2014/0288956 A1    Sep. 25, 2014

Related U.S. Application Data

(63) Continuation of application No. 12/181,971, filed on Jul. 29, 2008, now Pat. No. 8,781,848, which is a (Continued)

(51) Int. Cl.
*G06Q 50/00* (2012.01)
*G06F 19/00* (2018.01)
(Continued)

(52) U.S. Cl.
CPC ..... *G06F 19/3456* (2013.01); *G06Q 10/0631* (2013.01); *G06Q 50/22* (2013.01)

(58) Field of Classification Search
CPC .......... A61N 1/08; G06F 17/30; G06F 19/30; G06F 19/32; G06F 19/321; G06F 19/324;
(Continued)

(56) References Cited

U.S. PATENT DOCUMENTS 3,517,450 A    6/1970 Greco
3,921,196 A   11/1975 Patterson
(Continued)

FOREIGN PATENT DOCUMENTS

EP    0297780 A2   1/1989
JP    3218741 A    9/1991
(Continued)

OTHER PUBLICATIONS

Speedie, S.M., et al., "Mentor: Integration of an Expert System with a Hospital Information System," SCAMC, Inc., pp. 220-224, 5 pages.
(Continued)

*Primary Examiner* — Tran N Nguyen
(74) *Attorney, Agent, or Firm* — Lewis Rice LLC

(57) ABSTRACT

Systems and methods for providing targeted content to a patient who has received a prescription for medication. The systems and methods generally provide the content prior to the Point of Sale (POS) of the actual prescription to allow patients to review the content and possibly act on it prior to actually obtaining the medication. Depending on embodiment, the content may be provided by a pharmacy at or around the time of dispensing or by a physician at or around the time of prescribing.

15 Claims, 16 Drawing Sheets

Related U.S. Application Data continuation-in-part of application No. 12/054,066, filed on Mar. 24, 2008, now Pat. No. 8,615,406, which is a continuation of application No. 11/280,438, filed on Nov. 16, 2005, now Pat. No. 8,533,004, which is a continuation of application No. 11/222,699, filed on Sep. 9, 2005, now abandoned.

(60) Provisional application No. 60/608,587, filed on Sep. 10, 2004.

(51) Int. Cl.
*G06Q 50/22* (2018.01)
*G06Q 10/06* (2012.01)
*G06Q 10/00* (2012.01)

(58) Field of Classification Search
CPC .... G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; G06Q 10/10; G06Q 40/08; G06Q 50/22; G06Q 50/24; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/14; G16H 70/60; G16H 80/00
USPC ............................................................. 705/2
See application file for complete search history.

(56) References Cited

U.S. PATENT DOCUMENTS

| | | |
|---|---|---|
| 4,280,193 A | 7/1981 | Baun et al. |
| 4,491,725 A | 1/1985 | Pritchard |
| 4,766,542 A | 8/1988 | Pilarczyk |
| 4,847,764 A | 7/1989 | Halvorson |
| 4,910,672 A | 3/1990 | Off et al. |
| 5,088,051 A | 2/1992 | Forsythe et al. |
| 5,277,188 A | 1/1994 | Selker |
| 5,410,704 A | 4/1995 | Norden-Paul et al. |
| 5,454,066 A | 9/1995 | Tsai |
| 5,454,067 A | 9/1995 | Tsai |
| 5,459,306 A | 10/1995 | Stein et al. |
| 5,558,638 A | 9/1996 | Evers et al. |
| 5,608,639 A | 3/1997 | Twardowski et al. |
| 5,612,527 A | 3/1997 | Ovadia |
| 5,642,906 A | 7/1997 | Foote et al. |
| 5,644,723 A | 7/1997 | Deaton et al. |
| 5,664,073 A | 9/1997 | Faes et al. |
| 5,704,609 A | 1/1998 | Mandel et al. |
| 5,737,539 A | 4/1998 | Edelson et al. |
| 5,758,095 A | 5/1998 | Albaum et al. |
| 5,822,735 A | 10/1998 | DeLapa et al. |
| 5,827,180 A | 10/1998 | Goodman |
| 5,832,457 A | 11/1998 | O'Brien et al. |
| 5,833,599 A | 11/1998 | Schrier et al. |
| 5,845,255 A | 12/1998 | Mayaud |
| 5,855,395 A | 1/1999 | Foote et al. |
| 5,864,675 A | 1/1999 | Booth, Jr. et al. |
| 5,883,370 A | 3/1999 | Walker et al. |
| 5,884,271 A | 3/1999 | Pitroda |
| 5,930,764 A | 7/1999 | Melchione et al. |
| 5,954,640 A | 9/1999 | Szabo |
| 6,009,411 A | 12/1999 | Kepecs |
| 6,014,631 A | 1/2000 | Teagarden et al. |
| 6,014,634 A | 1/2000 | Scroggie et al. |
| 6,026,370 A | 2/2000 | Jermyn |
| 6,055,510 A | 4/2000 | Henrick et al. |
| 6,067,524 A | 5/2000 | Byerly et al. |
| 6,070,147 A | 5/2000 | Harms et al. |
| 6,075,971 A | 6/2000 | Williams et al. |
| 6,076,068 A | 6/2000 | DeLapa et al. |
| 6,112,182 A | 8/2000 | Akers et al. |
| 6,119,933 A | 9/2000 | Wong et al. |
| 6,182,050 B1 | 1/2001 | Ballard |
| 6,185,541 B1 | 2/2001 | Scroggie et al. |
| 6,230,199 B1 | 5/2001 | Revashetti et al. |
| 6,236,977 B1 | 5/2001 | Verba et al. |
| 6,240,394 B1 | 5/2001 | Uecker et al. |
| 6,266,648 B1 | 7/2001 | Baker, III |
| 6,304,849 B1 | 10/2001 | Uecker et al. |
| 6,307,958 B1 | 10/2001 | Deaton et al. |
| 6,317,719 B1 | 11/2001 | Schrier et al. |
| 6,327,574 B1 | 12/2001 | Kramer et al. |
| 6,334,108 B1 | 12/2001 | Deaton et al. |
| 6,356,873 B1 | 3/2002 | Teagarden et al. |
| 6,564,121 B1 | 5/2003 | Wallace et al. |
| 6,618,504 B1 | 9/2003 | Yoshino |
| 6,654,724 B1 | 11/2003 | Rubin et al. |
| 6,715,796 B2 | 4/2004 | Foote et al. |
| 6,988,075 B1 | 1/2006 | Hacker |
| 7,058,584 B2 | 6/2006 | Kosinski et al. |
| 7,154,397 B2 | 12/2006 | Zerhusen et al. |
| 7,230,529 B2 | 6/2007 | Ketcherside, Jr. et al. |
| 7,246,150 B1 | 7/2007 | Donoho et al. |
| 7,267,278 B2 | 9/2007 | Lammle |
| 7,286,996 B1 | 10/2007 | Fiedotin et al. |
| 7,286,997 B2 | 10/2007 | Spector et al. |
| 7,309,001 B2 | 12/2007 | Banfield et al. |
| 7,433,828 B2 | 10/2008 | Brinkman et al. |
| 8,121,868 B1 | 2/2012 | Grady et al. |
| 8,452,618 B2 | 5/2013 | Grady et al. |
| 8,533,004 B1* | 9/2013 | Grady et al. ................. 705/2 |
| 2001/0017817 A1* | 8/2001 | De La Huerga ............ 368/10 |
| 2001/0032099 A1 | 10/2001 | Joao |
| 2002/0022973 A1 | 2/2002 | Sun et al. |
| 2002/0029223 A1 | 3/2002 | Rice et al. |
| 2002/0032582 A1 | 3/2002 | Feeney, Jr. et al. |
| 2002/0032583 A1 | 3/2002 | Joao |
| 2002/0065758 A1 | 5/2002 | Henley |
| 2002/0069085 A1 | 6/2002 | Engel et al. |
| 2002/0077849 A1 | 6/2002 | Baruch et al. |
| 2002/0109861 A1 | 8/2002 | LeClair et al. |
| 2002/0116227 A1 | 8/2002 | Dick |
| 2003/0018495 A1 | 1/2003 | Sussman |
| 2003/0050799 A1 | 3/2003 | Jay et al. |
| 2003/0074234 A1 | 4/2003 | Stasny |
| 2003/0216981 A1 | 11/2003 | Tillman |
| 2004/0162835 A1 | 8/2004 | Ghouri |
| 2004/0193454 A1 | 9/2004 | Foote et al. |
| 2005/0049746 A1 | 3/2005 | Rosenblum |
| 2005/0069103 A1 | 3/2005 | DiVenuta et al. |
| 2005/0182656 A1 | 8/2005 | Morey |
| 2006/0136272 A1 | 6/2006 | Rubsamen |
| 2006/0247968 A1 | 11/2006 | Kadry |
| 2006/0261145 A1 | 11/2006 | Robertson et al. |
| 2006/0266826 A1 | 11/2006 | Banfield et al. |
| 2006/0287886 A1 | 12/2006 | Kitazawa |
| 2007/0124173 A1 | 5/2007 | Morag et al. |
| 2007/0219822 A1 | 9/2007 | Godwin et al. |
| 2013/0013332 A1 | 1/2013 | Frieder et al. |

FOREIGN PATENT DOCUMENTS

| | | |
|---|---|---|
| JP | 7028901 A | 1/1995 |
| JP | 8235273 A | 9/1996 |
| WO | 199506296 A1 | 3/1995 |
| WO | 199510813 A1 | 4/1995 |
| WO | 199634348 A1 | 10/1996 |

(56) References Cited

FOREIGN PATENT DOCUMENTS

| WO | 200106433 A1 | 1/2001 |
|---|---|---|
| WO | 2003085577 A1 | 10/2003 |
| WO | 2006036712 A2 | 4/2006 |

OTHER PUBLICATIONS

Barer, M.L., Bhatia, V., Stoddart, G.L., and Evans, R.G., "The Remarkable Tenacity of User Charges: A Concise History of the Participation, Positions, and Rationales of Canadian Interest Groups in the Debate over 'Direct Patient Participation' in Health Care Financing," Dec. 1993, p. 1-32, 32 pages.

Erstad, B.L., and Murphy, J.E., "Developing Critical Interaction Skills in Students: Debating Clinical Pharmacokinetic Controversies," American Journal of Pharmaceutical Education, 1994, p. 440-445, vol. 58, 6 pages.

Society of Critical Care Medicine, "Guidelines for Intensive Care Unit Design," Critical Care Medicine, Mar. 1995, p. 582-588, 11 pages.

"Eckerd bolsters retail technology," Chain Drug Review, May 20, 1996, Racher Press Inc., 3 pages.

Schiff, G.D., et al., "Computer prescribing: Building the electronic infrastructure for better medication usage," JAMA, Apr. 1, 1998, Abstract, vol. 279, Issue 13, Chicago, IL, 1 page.

Ingenerf, J., "Telemedicine and Terminology: Different Needs of Context Information," IEEE Transactions on Information Technology in Biomedicine, Jun. 1999, pp. 92-100, vol. 3, Issue 2, 9 pages.

"Telecommunication Standard," National Counsel for Prescription Drug Programs, Sep. 1999, Version 5, Release 1, 97 pages.

Dufour, J., et al., "Coupling computer-interpretable guidelines with a drug-database through a web-based system—The PRESGUID project," BMC Medical Informatics and Decision Making, Mar. 2, 2004, pp. 1-12, vol. 4, Issue 2, BioMed Central Ltd., 12 pages.

"Basic Guide to Standards," National Counsel for Prescription Drug Programs, May 2004, 16 pages.

"Envision Pharmaceutical Services Selects MedInitiatives to Deliver Health Care Analytics," Business Wire, Aug. 9, 2005, 3 pages.

Siegel, E.R., et al., "Information Rx: Evaulation of a new informatics tool for physicians, patients, and libraries,"The Institute of Engineering and Technology, Information Services & Use, 2006, Abstract, vol. 26, Issue 1, Netherlands, 1 page.

Smith, A.D., "Barriers to accepting e-prescribing in the USA," International Journal of Health Care Quality Assurance, 2006, p. 158-180, vol. 19, No. 2, Emerald Group Publishing Limited, 11 pages.

"System and Method for Performing Pharmacovigilance," printed on Jan. 17, 2013, 110 pages.

Timmreck, E. M., "Computer Selection Methodology," Computing Surveys, Dec. 1973, pp. 199-222, vol. 5, No. 4.

* cited by examiner

SYSTEMS AND METHODS FOR PROVIDING AN INDUCEMENT OF A PURCHASE IN CONJUNCTION WITH A PRESCRIPTION

CROSS REFERENCE TO RELATED APPLICATION(S)

This Application is a Continuation of U.S. patent application Ser. No. 12/181,971 filed Jul. 29, 2008 and currently pending, which is a Continuation-in-Part (CIP) of U.S. patent application Ser. No. 12/054,066 filed Mar. 24, 2008, now U.S. Pat. No. 8,615,406, which is in turn a Continuation of U.S. patent application Ser. No. 11/280,438, filed Nov. 16, 2005, now U.S. Pat. No. 8,533,004, which is in turn a Continuation of U.S. patent application Ser. No. 11/222,699 filed Sep. 9, 2005, now abandoned, which in turn claims the benefit of U.S. Provisional Patent Application 60/608,587 filed Sep. 10, 2004. The entire disclosure of all these documents is herein incorporated by reference.

BACKGROUND

1. Field of the Invention

This disclosure relates to systems for providing content to patients who have been prescribed medications, specifically to systems which can provide content at the point of prescribing of the medication and may provide ongoing dialogue between a patient and a medication provider.

2. Description of the Related Art

Advances in pharmaceuticals in recent times have led to the effective treatment for many disorders which only a few years ago had no available treatment. While these medications can be invaluable to those who need them, they can also be difficult to use correctly and may be benefited in their efficacy by other changes in a patient's lifestyle outside the control of their physician. Many medications today are not single dose wonder drugs, but require adherence to a schedule of medication and lifestyle adjustment to be most effective. Sometimes these schedules require a patient to follow complex usage instructions with multiple medications taken at regular time intervals.

One of the biggest problems with the use of modern pharmaceuticals is to make sure that the patient uses them correctly so that they are safe and effective. Further, a patient often needs to be educated that the medication may not solve the underlying problem without the patient making more fundamental changes to their lifestyle. After a medication is dispensed, neither a pharmacist, physician, or pharmaceutical manufacturer has much control over the actions of a patient and incorrect use of the medication can not only result in ineffective treatment, but a condition becoming resistant to a medication. The misuse of medications can arise from a variety of causes ranging from persons being unable to maintain a medication's prescribed schedule, to purposefully taking smaller doses to make medications last longer, to people simply misunderstanding complicated usage instructions, to medications lacking efficacy and requiring adjunct or alternate medications, to medications being resold on secondary markets or otherwise abused.

To deal with these and other problems, pharmaceutical manufacturers and physicians have been trying to provide better information to patients so that patients understand how the medications need to be used to be most effective and how their therapies can be managed most effectively. Further, there is a recognition in the medical community that a medication may not be a "magic bullet" to solve a condition, but may be an aid, that when combined with lifestyle changes, can get a patient to recover from the condition quicker, or can make it easier for them to live with the condition.

The provision of information to the ultimate patient of the medication has proven to be a problematic issue, however. Often medication information is confusing and difficult to read. Further, informational packets provided to a doctor or pharmacist by a pharmaceutical manufacturer to be provided to a patient may be misplaced or not given out correctly. Further, recently both pharmacists and physicians have been subjected to decreased reimbursements from insurance companies and other payors for their services. This has resulted in their need to increase the volume of cases they handle to maintain profits at a functional level, which has, in turn, resulted in them being unable to spend as much time with each patient and therefore less time discussing information related to indicated medications with patients. For these reasons, among others, it is desirable to provide information in a form where there is little chance for human forgetfulness in providing the information with the medication whenever possible, and in a form that allows pharmacists and physicians to provide more information in less time by providing information that the patient can study at home or at another convenient time.

Another issue related to modern medication is the increase in generics and competitive brands and the need for original medication manufacturers to brand a medication and build customer loyalty to be able to recoup research and development expenses. Modern medications can require a massive investment for research and development as well as large investments for production and distribution. Further, educational programs for physicians to instruct them in how to provide the medication to appropriate patients also require a large investment by the medication manufacturer. These costs are generally intended to be made up by medication sales. However, if another brand enters the market which is able to maintain lower costs by utilizing the investment already made by the first medication company, the original innovator may be unable to effectively compete leading to there being less development as investments cannot be returned.

Medication companies can attempt to recoup investments by patenting medications, but also will utilize branding to try and distinguish their product from other competitive products. Branding with trademarks is a well recognized process in all facets of goods. However, branding requires investments in advertising to bring the brand to the awareness of the consumer. Further, most pharmaceutical companies do not have a single brand, but utilize many brands. Building customer loyalty to products can also help to offset costs by having a pharmaceutical consumer not only purchase a particular product from the manufacturer, but to also purchase other products that s/he may need as well.

Provision of information related to the drug can be beneficial if provided at the pharmacy. Such benefits can also carry over into over-the-counter (OTC) medications. OTC products can be useful, or harmful, in combination with prescription drugs, and, in some cases, in place of prescription drugs. OTC products can also be useful in treating side effects from prescription drug use.

In order to provide usage and other information to medication consumers regarding both prescription and OTC products at the pharmacy, many pharmacies have adopted systems for providing pharmacy information sheets such as those described in U.S. Pat. Nos. 6,240,394 and 6,067,524, the entire disclosures of which are herein incorporated by reference, to use with the distribution of medications. The problem with these systems, however, is that they are cumbersome to pharmacists and require the inclusion of significant additional computer hardware which takes up space at the pharmacy. Further, these "add-on" systems can break down leaving the systems non-functional until service technicians outside the pharmacy come in and repair or replace them. Further, these systems impose capital expenses, increased maintenance, and other problems on those providing the pharmacy information sheets which necessarily increase the costs of providing the services. The systems are generally redundant between pharmacies and are operationally inefficient as the systems rely on mechanisms which provide for unnecessary complexity.

The systems also only provide information at the point of sale of the medication. This is often too late as by the time the patient will review the material they have left the pharmacy and already own the medication.

SUMMARY

Because of these and other problems in the art, discussed herein are systems and methods for providing targeted material to a prescription medication patient which do not require significant hardware investment and provide for streamlined provision of material in a way which is more transparent to the pharmaceutical provider. The systems may also provide information to the patient prior to the patient leaving the pharmacy or physician's office with the medication. In this way, the patient will often be both a captive audience for the information and will have ready access to a physician or pharmacist who can answer any questions that may arise from the content.

There are described herein, among other things, a system for generating information at a physician's office for a patient related to a prescribed medication, the system comprising: a physician's server being attached to the Internet, the physician's server being provided with prescription information, as part of a medication being prescribed to a patient; content requesting software running on the physician's server; an auxiliary computer, the auxiliary computer also attached to the Internet and capable of receiving information from the physician's server; selection software running on the auxiliary computer; and a bridge server attached to the Internet and capable of requesting information from the auxiliary computer and sending instructions to a printer to print content; wherein the content requesting software forms a first data structure including at least a portion of the prescription information and transmits the first data structure to the auxiliary computer; wherein the selection software receives the first data structure and from at least a portion of the first data structure selects content for the patient; wherein the auxiliary computer creates and holds a second data structure indicative of the content; wherein the bridge server periodically requests second data structures from the auxiliary computer; wherein, upon receipt of such a request from the bridge server, the auxiliary computer forwards the second data structure to the bridge server; and wherein, in response to the second data structure being received, the bridge server causes the content to be printed.

In an embodiment of the system the second data structure comprises the content. In an alternative embodiment, the second data structure references content on the bridge server.

In another embodiment of the system, the bridge server reformats the second data structure into material understood by a printer.

In another embodiment of the system, the content functions to induce the patient to purchase a particular product, such as, but not limited to, a particular brand of medication.

In another embodiment, the system further comprises a physician's device, such as, but not limited to, a handheld computer, the physician's device being provided the prescription information from a physician and transferring the prescription information to the physician's server. The physician's device may also indicate when the content is printed.

In another embodiment of the system, the physician's server is loaned to the physician's office such as through a lease arrangement. It may also comprise an electronic prescribing vendor's server.

In a still further embodiment, the physician's server comprises a web browser accessing an electronic prescribing vendor's server acting as an application service provider (ASP).

In a still further embodiment of the system, the bridge server queues content to be printed by the printer.

DESCRIPTION OF PREFERRED EMBODIMENT(S)

Figure 1:
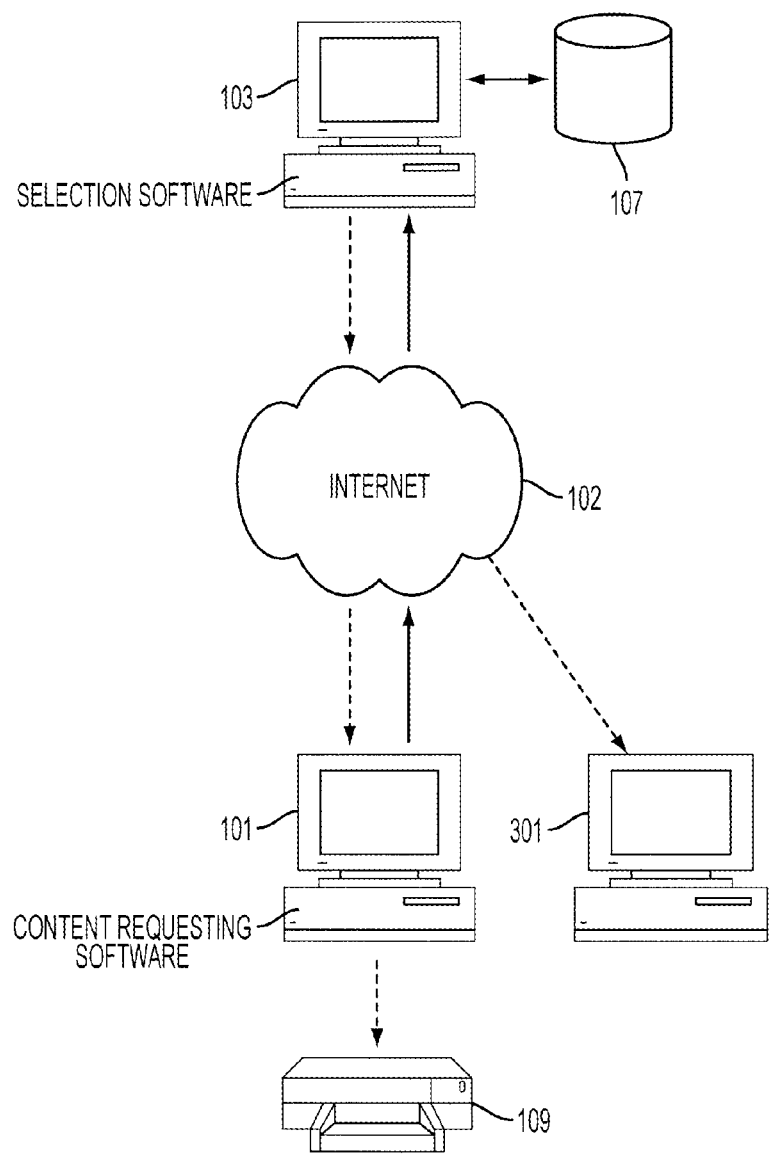
FIG. 1 Provides a block diagram of an embodiment of a patient communication system utilizing information provision at a pharmacy.

The systems and methods discussed herein are principally designed for providing targeted material to a prescription medication patient prior to their obtaining the actual medication and in an embodiment, as part of an ongoing dialogue with the patient. This material is generally geared specifically to the patient, their condition, and the medications they have been prescribed and can, among other things, help to provide information about a particular medication brand, provide information about related products made by a similar company whether prescription or over-the-counter (OTC), provide for additional patient information, provide information about or promote an adjunct application for a medication, or provide for suggestions or reminders of actions to be performed by the patient to improve medication efficacy such as, but not limited to, lifestyle changes. This material, regardless of type, is generally referred to herein as "content." Content is intended, in an embodiment, to provide for an effective dialogue to the patient at various stages of medication use. The content may be provided by any party involved in any way with the medication or system.

A "patient" as discussed herein will specifically refer to an individual who has been, or will be, prescribed a particular prescription medication for their, or another's, use. The patient may not have actually obtained or taken the prescription medication before, or may be a regular patient of the medication. The patient will, however, have been, or will soon be, prescribed the medication as treatment for a particular condition which the patient is presumed to have. It should be recognized, however, that in an embodiment, the patient may not have the condition or may be attempting to obtain unauthorized medications through a falsified prescription or similar contrivance.

The "medication" will generally be presumed to be a pharmaceutical drug available by prescription. However, the medication is not limited to drugs but can include other items such as, but not limited to, supplements, ointments, placebos, devices, or any other materials available by prescription. Therefore, the term "medication" is used broadly to refer to objects which are prescribed or otherwise indicated for use by the patient in treatment of the condition.

The patient will generally interact with two individuals during the prescription process. The first of these will be the individual who assigns the prescription to the patient. This individual will be referred to herein as a "physician"; however, one of ordinary skill in the art would recognize that this term is not intended to be limited to doctors, but could encompass any individual who is able to prescribe any medications. Further, tasks discussed herein as being performed by a physician could also be performed by any member of a physician's staff authorized to perform that action. This could include but is not limited to, a nurse, a physician's assistant, a technician, an intern, a resident, a medical student, a secretary, or any other individual tasked by the physician to carry out the action. These individuals are all, therefore, included within the definition of physician for the purposes of this disclosure.

The second individual is the one who dispenses the prescription or otherwise physically prepares the medication to be provided to the patient. This person is referred to herein as the "pharmacist." Again, it should be recognized that the term is not limited to those who are licensed pharmacists but to anyone who can legally fill a prescription. Again, tasks discussed herein as being performed by a pharmacist could also be performed by any member of a pharmacist's staff authorized to perform that action. This could include but is not limited to, a technician, an intern, a pharmaceutical student, a secretary, or any other individual tasked by the pharmacist to carry out the action. These individuals are all, therefore, included within the definition of pharmacist for the purposes of this disclosure. It should also be recognized that in some cases the physician and the pharmacist may be the same person.

The system has two principle points of contact with the patient depending on the embodiment. In some embodiments, the system utilizes the patient's contact with the pharmacist dispensing the medication in accordance with the prescription as the point of contact. Other embodiments utilize the patient's contact with the physician providing the prescription as the point of contact. Still further embodiments utilize both these points of contact as well as direct contact. Any embodiment may also utilize ongoing dialogue with the patient outside of their contact with either the physician or pharmacist as an additional point of contact.

The embodiment of FIG. 1 is designed so content is provided at the point of medication dispensing (at the pharmacy). It, therefore, is generally intended to provide the content at a pharmacy location so that the information may be provided to the patient in conjunction with the physical medication also being provided at the same location. Supplying information at this time is beneficial as the patient will be provided with the physical medication and the content in close proximity to each other which places the two items together and makes it harder for the patient to misplace the content later. They will preferably be provided with the content prior to actually getting the medication so that they can review it while waiting for the medication to be prepared.

In this embodiment, the layout comprises a pharmacy computer (101) which is under the control of the pharmacist dispensing the medication. The pharmacy computer (101) will generally be a computer previously in use by the pharmacist for preparing prescriptions and will include software for preparing and filling prescriptions. This software may be designed to provide for clinical review of medications, to provide for necessary record keeping for pharmacy transactions, may provide for the printing of pharmacy container labels, or any other functionality commonly in a pharmacy computer (101) of the prior art.

The pharmacy computer (101) will also include hardware and/or software allowing access to the Internet (102) or other network by any mechanism currently known or later discovered including, but not limited to, through a modem and phone line, a Digital Subscriber Line (DSL) connection, a cable modem, a T1 or T10 high speed connection, a wireless connection, or any other connection. Generally, Internet (102) service will be provided by an Internet Service Provider (ISP). This communication software and hardware may be provided standard with the pharmacy computer (101), may have been added for other reasons, or may be provided as part of an embodiment of the system for providing content.

Throughout this disclosure, the term "computer" will be used to describe hardware which implements functionality of various systems. The term "computer" is not intended to be limited to any type of computing device but is intended to be inclusive of all computational devices including, but not limited to, processing devices or processors, personal computers, work stations, servers, clients, portable computers, and hand held computers. Further, each computer discussed herein is necessarily an abstraction of a single machine. It is known to those of ordinary skill in the art that the functionality of any single computer may be spread across a number of individual machines. Therefore, a computer, as used herein, can refer both to a single standalone machine, or to a number of integrated (e.g. networked)

machines which work together to perform the actions. In this way the functionality of a pharmacy computer may be at a single computer, or may be a pharmacy network whereby the functions are distributed. Further, the term "software" refers to code objects, logic, or command structures, written in any language and executable in any environment designed to be executed by or on a computer. It should be recognized that software functionality can be hardwired onto a chip or into other hardware while still considering it software within the meaning of this disclosure.

In order to provide for the content, the pharmacy computer (101) will have additional software installed thereon to carry out the arrangement and transfer of information with a remote auxiliary computer (103) as discussed below. This software, which is called the "content requesting software" will preferably be entirely contained on the pharmacy computer (101) and will operate to form the first data structure and transmit the first data structure to the auxiliary computer (103). In some embodiments, the content requesting software will also receive a second data structure from the auxiliary computer (103), and transmit content to a pharmacy printer (109).

The content requesting software will preferably be installed on a hard drive or other memory device associated with or accessible by the pharmacy computer (101) so that the content requesting software can be executed by the pharmacy computer (101). It is preferred that the content requesting software be operable in a standard operating environment (such as, but not limited to, Windows™, MacOS™, Unix™, or Linux™-based operating systems) and it is more preferred that the content requesting software be able to operate in conjunction with, and be integrated into, the software previously on the pharmacy computer (101) for carrying out prior art pharmacy transactions. In an embodiment, the content requesting software is designed to integrate with the software for pharmacy functions and may be considered a plug-in or upgrade to the software previously provided for pharmacy functions. In an embodiment, the content requesting software will operate autonomously or semi-autonomously requiring little or no additional input from the pharmacist in order to carry out its functions. In this way it operates relatively transparently to the pharmacist.

It should be recognized that the content requesting software is preferably integrated with the operation of the pharmacy computer (101) in the performance of the pharmacy computer's prior tasks at the pharmacy. The content requesting software does not comprise any type of external "capture" system using output generated by the pharmacy computer (101), but instead operates as a part of the pharmacy computer's (101) operation and on the pharmacy computer (101) to integrate with existing functionality.

The system also comprises an auxiliary computer (103) located physically remote from the pharmacy computer (101), specifically not in the actual pharmacy, and not under the control of the pharmacist dispensing the prescription. Preferably, the auxiliary computer (103) will be in a physically secured location. The auxiliary computer (103) also includes hardware and software allowing access to the Internet (102) by any mechanism currently known or later discovered such as, but not limited to, a modem and phone line, a Digital Subscriber Line (DSL) connection, a cable modem, a T1 or T10 high speed connection, a wireless connection, or any other connection. The auxiliary computer (103) is generally a server type of computer capable of receiving and transmitting information via a network. In particular, the auxiliary computer (103) includes software designed to receive a first data structure from the pharmacy computer (101) sent by the content requesting software and to respond to that first data structure with a second data structure which is understood by other computer(s) designed to receive it whether the pharmacy computer (101) or another computer. This software is called "selection software."

Generally, a single auxiliary computer (103) will be presumed to communicate with a plurality of pharmacy computers (101) via the Internet. However, there may be more than one auxiliary computer (103) configured to communicate with the plurality of pharmacy computers (101). Therefore, the auxiliary computers (103) and pharmacy computers (101) may be arranged in any form of server/client relationship, as that term is understood by those of ordinary skill in the art, with the auxiliary computers (103) generally acting as servers and the pharmacy computers (101) generally acting as clients. The auxiliary computer (103) may be a stand alone machine, or may have access to external resources such as an external memory or database (107). In an embodiment, multiple auxiliary computers (103) have access to a shared memory such as database (107).

In the embodiment of FIG. 1, the pharmacy computer (101) can transmit information on a patient's prescription and on the patient to the auxiliary computer (103) via the Internet as a first data structure. The first data structure will generally comprise a transmission sent via a standard Internet protocol such as hypertext transfer protocol (http) or any other protocol used on the Internet whether known now or later discovered. The solid line of FIG. 1 generally shows the path of the first data structure in this embodiment. The first data structure includes all necessary information for use by the auxiliary computer (103) to identify characteristics of the dispensing activity which are to be used by the auxiliary computer (103). Upon receipt of the first data structure at the auxiliary computer (103), selection software on the auxiliary computer (103) may use some or all of the information in the first data structure to select content targeted to the patient. If there is content selected, the auxiliary computer (103) will either send the content to the pharmacy computer (101) or may send an identifier to identify particular content stored on the pharmacy computer (101). Whichever is sent, this transmission comprises a second data structure and is shown by the dashed line in FIG. 1.

There is also a pharmacy printer (109) physically co-located with the pharmacy computer (101), specifically in the pharmacy, and under the control of the pharmacist dispensing the prescription. The pharmacy printer (109) may be any type of printer capable of rendering paper versions of electronic data and will be used to fulfill any needed print requests from the pharmacy computer (101). Generally, the pharmacy printer (109) will be arranged to print vial labels, amongst other things, to aid the pharmacy in the dispensing process. The pharmacy printer (109) will generally be connected to the pharmacy computer (101) by a cable (104) such as, but not limited to, a serial, parallel, or similar cable or through a wireless interface such as infrared (IR). Alternatively, the pharmacy printer (109) may be connected to the pharmacy computer (101) via a Local Area Network (LAN) if the pharmacy printer (109) is shared by multiple pharmacy computers (101) co-located with each other. The content identified by the auxiliary computer (103) in the second data structure, will be sent to the pharmacy printer (109) by the pharmacy computer (101). This transmission will comprise a standard print task between a computer and a printer. The content will be formatted by the pharmacy computer (101) for printing in accordance with standard print formatting principles. The pharmacy printer (109) will generally print the content in a single-sided or double-sided format on paper provided at the pharmacy printer (109).

The auxiliary computer (103) may also be connected, via the Internet, to a computer or other system capable of receiving information directed to it from the Internet (the patient access computer (301)). This may be a computer capable of receiving email, automated messaging, or voice transmissions, or may be another computing or processing device such as a cellular telephone, BlackBerry™ device, or personal digital assistant (PDA) capable of connecting to the Internet or receiving packetized data. The patient access computer (301) can be accessed directly by the patient, generally via a secured connection, and may be accessed directly or over a network such as the Internet.

Figure 2:
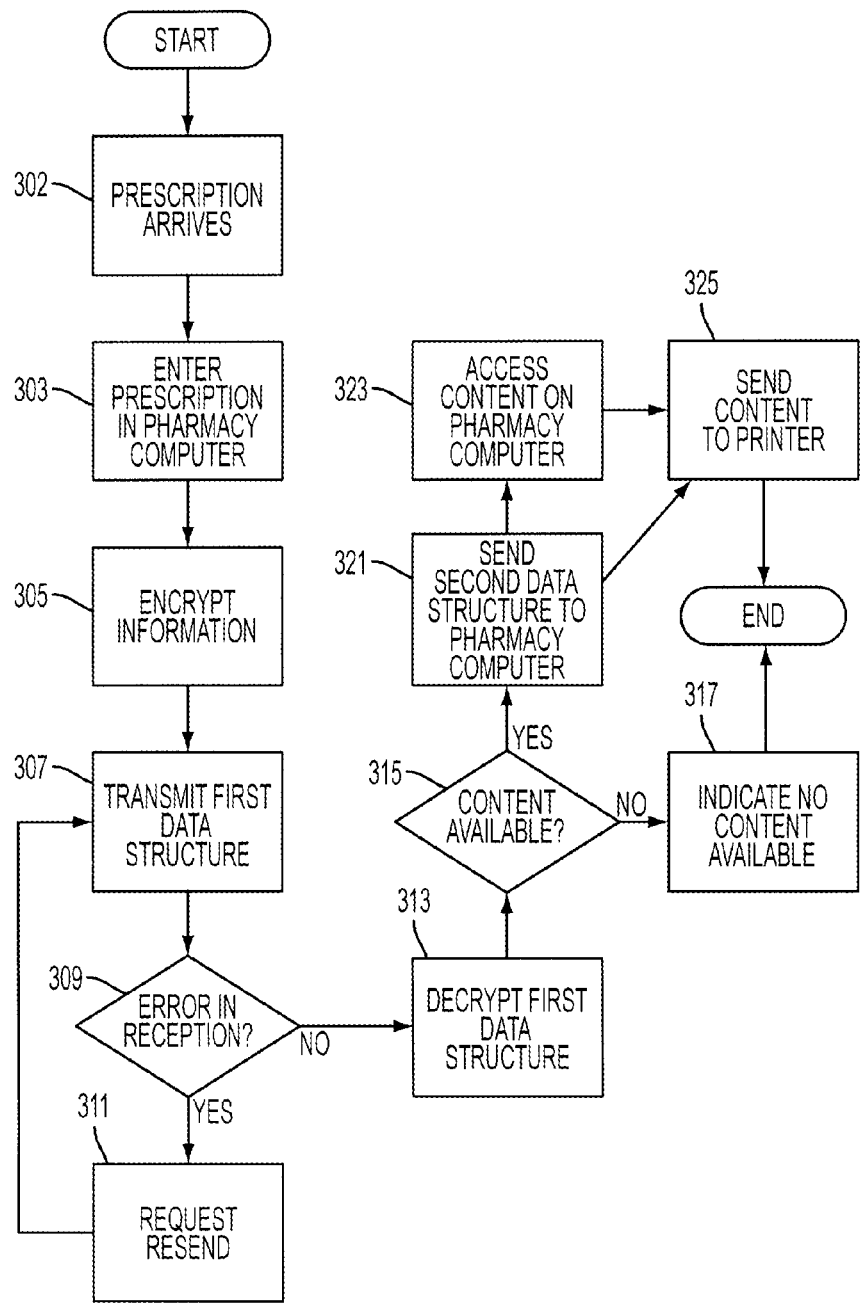
FIG. 2 Provides a flowchart of steps in an operation of the embodiment of FIG. 1.

An embodiment of the operation of the embodiment of the system shown in FIG. 1 follows the flowchart of steps shown in FIG. 2. While this order of steps is intended to be exemplary, it is in no way limiting to the particular order of steps provided. A patient will generally arrive at the pharmacy in step (302) to request a prescription be dispensed for which they will generally have a written prescription paper from their physician. The prescription may alternatively have been electronically transmitted to the pharmacy by the physician. This may be a new or renewed prescription. Alternatively, the patient may be picking up a refill of a prescription already in possession of the pharmacist. In this case, the patient will not provide the prescription, but will have identified themselves to the pharmacist and the pharmacist will confirm that that patient has an available refill already on record at the pharmacy.

Regardless of the method that the prescription is provided to the pharmacy, the pharmacist will enter the information from the prescription into the pharmacy computer (101) in step (303) if it has not already been so provided. The pharmacy computer (101), once provided with the prescription information, will carry out any manipulations on that information as it normally would and will generally store that information to an associated memory.

The entered information will generally include any or all of, but is not limited to: The National Drug Code (NDC) for the prescription, the patient's age, patient's gender, patient ID (such as a name and/or identifying number), patient contact information, physician identifier, prior patient behavioral data, whether it is a new or refilled prescription, or any other information of the type traditionally entered by a pharmacist in preparation for dispensing a prescription. There also may be information gathered which is not normally collected but is available to the pharmacist from the patient and useful in selecting content.

Once the information is entered, the pharmacy computer (101) will perform its normal actions to allow the pharmacist to fill the prescription. In addition, the content requesting software on the pharmacy computer (101) will perform additional steps to provide for selection of the content. In particular, the content requesting software will gather data from the information entered as a part of this pharmacy transaction and encrypt in step (305) some or all of the data gathered, and possibly other information already on the pharmacy computer (101) such as, but not limited to, the name of the pharmacy, the address of the pharmacy, and the store number of the pharmacy, and transmit the encrypted information in step (307) as a first data structure to the auxiliary computer (103) over the Internet. Encryption need not be used in an alternative embodiment. However, as the information sent would generally be considered to be confidential, it is preferred that a secure encryption method be used to prevent eavesdropping.

When the first data structure is received by the auxiliary computer (103), the auxiliary computer (103) in step (309) will generally confirm that the information received is without errors in transmission as is understood by those of ordinary skill in the art. If the receipt is not confirmed, the auxiliary computer (103) will request resending of the information in step (311). If the information is confirmed to be received, the auxiliary computer is step (313) will decrypt the first data structure and may then store some or all of the information therein in an associated memory or database (107). The database (107) may be either local on the auxiliary computer (107) such as an associated hard drive or may be located remotely such as on a network depending on the arrangement of the auxiliary computer (103). The database (107) may include other information about this patient received from prior transactions about this patient with the pharmacy computer (101) or with other pharmacy computers or other systems in communication with the auxiliary computer (103).

Based on the new information provided from the first data structure, possibly in conjunction with information already in the database (107), the selection software in step (315) will determine whether content or information should be provided to the specific patient. The availability of content will generally be determined by analyzing the information and any other information the auxiliary computer (103) has available on the patient to look for particular patterns or entries based on a predetermined set of search criteria located at the auxiliary computer (103). This may be a result of any pattern and content may be selected based on any number of pieces of information as specified by the selection software running on the auxiliary computer (103).

Once the selection software determines in step (315) if a particular pattern or entry exists which corresponds to particular content being appropriate for distribution to the patient, the content will be selected by the selection software. The content may be of any form and may include any information as discussed later.

If no content is available, the auxiliary computer (103) may send back to the pharmacy computer (101), via the Internet, an indicator that no content is available as in step (317) or the auxiliary computer (103) may simply do nothing within a prescribed time to indicate that no content is available to the pharmacy computer (101). If selection software determines that content is available, the auxiliary computer (103) may provide, via the Internet connection between the pharmacy computer (101) and the auxiliary computer (103), a second data structure to the pharmacy computer (101) as shown in step (321). The second data structure may comprise either the content in a form understandable by the content requesting software on the pharmacy computer (101) (such as, but not limited to, a file formatted for Microsoft Word™, or Adobe Acrobat™) or instructions to utilize particular content maintained in a memory cache at the pharmacy computer (101) or a third computer in communication therewith.

When the pharmacy computer (101) receives the second data structure from the auxiliary computer (103), the pharmacy computer (101) may also perform error checking in a similar fashion to that performed by the auxiliary computer (103) in steps (309) and (311). Once receipt is confirmed, if the second data structure comprises actual content, the content may be printed by the content requesting software, sending it to the pharmacy printer (109) via the print stream in step (325). If the pharmacy computer (101) receives instructions about the content to be used, the content requesting software may access the content in a local memory cache at the pharmacy computer (101) or other location accessible to the pharmacy computer (101) in step (323) and then send the content to the pharmacy printer (109) in step (325).

Regardless of which method is used for sending content to the pharmacy printer (109), the pharmacy printer (109), upon receiving the content, will print the content. Preferably, the printing will occur on a single sheet of standard paper forming an insert or reference sheet. The content may be combined with other information sent to the printer to be printed such as the medication monograph, receipt, or other counseling information provided by the pharmacy computer (101) in the course of a normal pharmacy transaction. The pharmacist will pick up the printed content either prior to or while preparing the medication. They may review the content, and will then generally place the content with the medication.

Alternatively, the pharmacist can provide the content to the patient while they are waiting for the prescription and before they have left the pharmacy drop-off window. The entirety of steps in FIG. 2 may be accomplished in a matter of seconds allowing the content to be distributed prior to filling the prescription. It should be recognized that in either case the content is prepared and provided in response to a request for dispensing of the medication, not the sale of the medication. This provides for content prior to completion of a pharmacy transaction. In most cases, the content will be provided with the medication with both items then being placed behind a counter or similar for later pickup by the patient or the content will be provided to the patient while they are waiting for the prescription to be dispensed. When the patient picks up their prescription and pays for it, the content will already be present with the medication or previously provided to them, it will not be generated in response to the sale of the medication.

This is an important distinction because the point of sale (POS) of the medication is often too late to provide the information. At the POS, the patient is completing the transaction and if material was to be printed, the patient would be forced to wait for the material to print after (or while) paying, which they may or may not choose to do as they have already obtained their medication and their ability to maintain confidentiality about the nature of their prescription with a pharmacist may be lost as a clerk or other employee may actually control the POS. Distributing the content at the point of dispensing provides for the material to already be present for review by the patient and pharmacist together while maintaining patient privacy (between patient and pharmacist) prior to completion of the sale. This also allows the patient to review the material before completing the sale which can allow the patient to determine if they would like to purchase additional products based on the content without having to carry out a second sales transaction or if there are concerns which may result in the sale not being completed. In the case where content can be provided prior to the patient commencing their waiting for the prescription, it also provides the content to the patient when they are at the pharmacy, generally with little or nothing to do, and the patient can read the content while waiting. Further, if the patient's use of additional non-prescription products or OTC medications is encouraged by the content, the patient can locate those products at the pharmacy while waiting, and can utilize information provided with the content in a discussion with the pharmacist without having to return to the pharmacy after obtaining their medication.

This arrangement also provides for a single transaction for the patient for both the medication and other related products whose use may be encouraged by the content, and the ability to have read the content and prepared any questions before purchasing the medication or leaving the pharmacy. These can improve the patient's willingness to follow through with the medication, for them to use the medication effectively, and can make it much easier for them to bring any questions or concerns to the pharmacist's attention at the time they purchase their medication.

Figure 3:
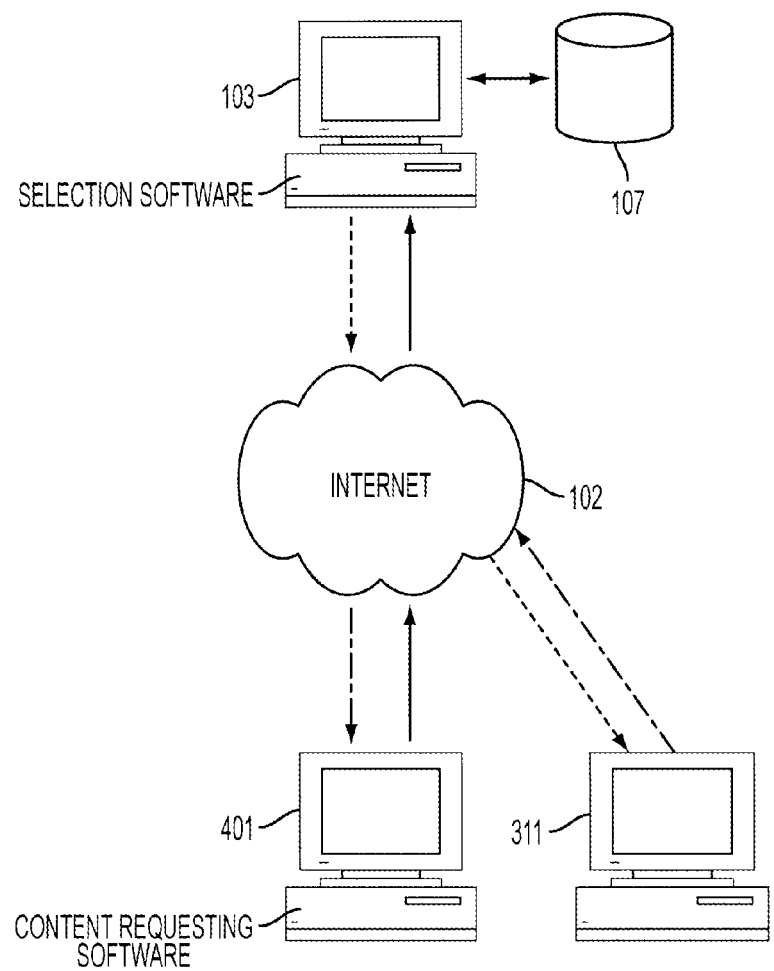
FIG. 3 Provides a block diagram of an embodiment of a patient communication system utilizing information provision via an Internet pharmacy prescription request.

FIG. 3 provides a block diagram of another embodiment of a system for providing information to the patient. In this system, the pharmacist is still used as the point of contact and the content is still generated at the point of dispensing; however, the pharmacy is presumed to be remote from the user who is connected to it via an Internet transaction. A similar embodiment would utilize phone or mail order transactions. In the particular embodiment of FIG. 3, the user is connected to an Internet connection and the pharmacy comprises a so-called "Internet pharmacy." This embodiment is similar to the embodiment of FIG. 1, and the detail of computers is not repeated due to the similarity. However, in this case, the patient will never actually go to the pharmacy but the prescription will be transmitted electronically, the medication will be dispensed remotely, and it will then, generally be mailed to them. Therefore, the provision of the content does not rely on printing at the pharmacy.

In this embodiment, the system will generally operate in a similar manner to the embodiment of FIG. 1, however, the information used to select content may be obtained directly from the patient as well as from the e-pharmacy computer (401). In particular, to transmit the prescription request to the e-pharmacy for dispensing, the patient will generally enter order information into a patient computer (311). The prescription information may be on the e-pharmacy computer (401) or may be provided to the e-pharmacy computer (401) by the patient (generally by mail) or directly from the physician or physician's electronic prescribing provider. This order information can be received by the content requesting software which will generally be running on the e-pharmacy's computer (401) which will receive the order. This is shown by the long dash short dash line in FIG. 3. Upon receipt, the content requesting software can send the first data structure to the auxiliary computer (103) in the same manner as it would from the standard brick-and-mortar pharmacy computer (101). The auxiliary computer (103) can then contact the patient computer (311) directly via the Internet, providing the content via email screen pops or another form as soon as the prescription is transmitted from the patient.

Figure 4:
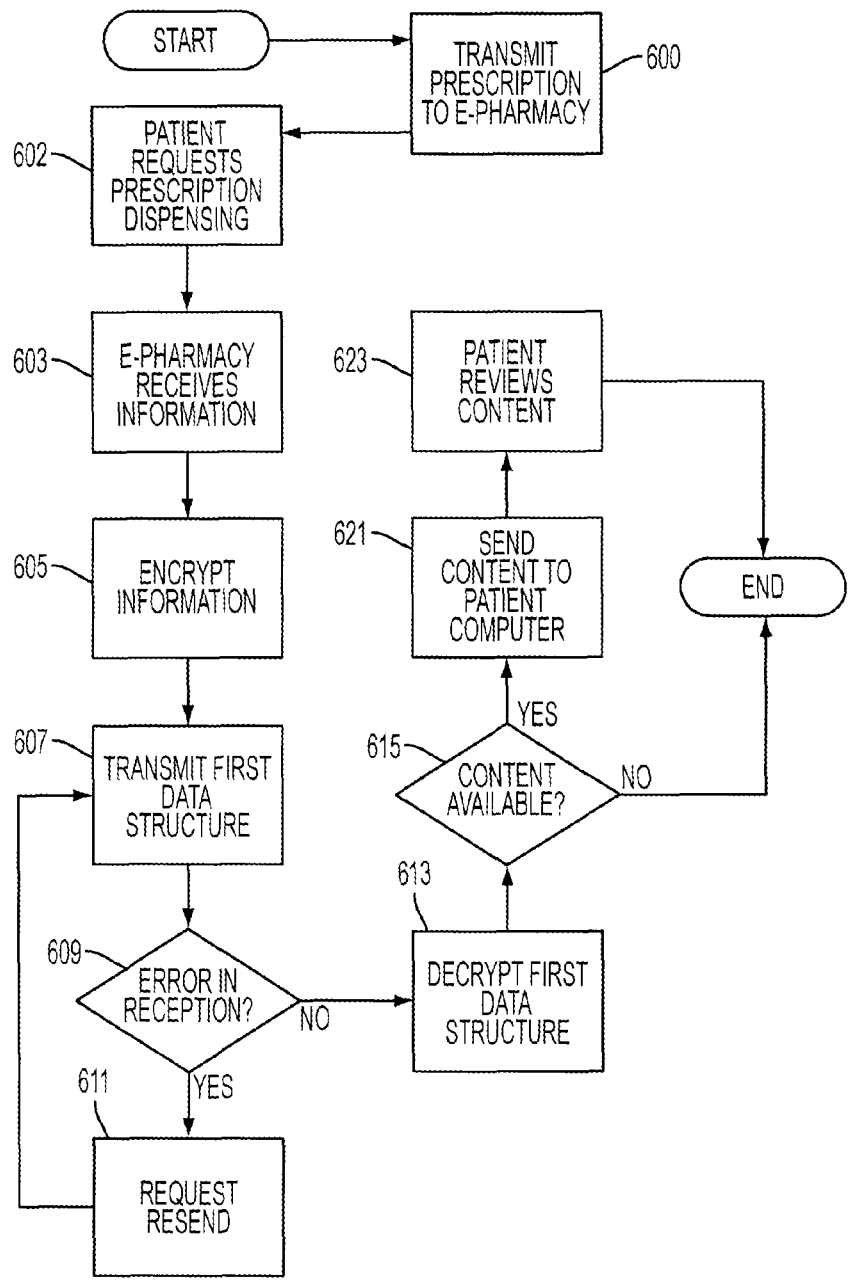
FIG. 4 Provides a flowchart of steps in an operation of the embodiment of FIG. 3

An embodiment of the operation of the embodiment of the system shown in FIG. 3 follows the flowchart of steps shown in FIG. 4. Once again, while this order of steps is intended to be exemplary, it is in no way limiting to the particular order of steps provided. In step (600) the physician or patient sends the prescription to the e-pharmacy such as by, but not limited to, fax, email, or mail. The patient in step (602) will electronically transmit information necessary to enable the e-pharmacy to dispense the prescription to the e-pharmacy computer (401) using standard electronic transmission mechanisms such as email or by filling out an online form. This information will be received by the e-pharmacy computer (401) in step (603). The e-pharmacy computer (401), once provided with the prescription information, will carry out any manipulations on that information as it normally would and will generally store that information to an associated memory.

The entered information may include any or all of the information provided in the embodiment of FIGS. 1 and 2. Once the information is received, the e-pharmacy computer (401) will perform its normal actions to allow filling of the prescription. In addition, the content requesting software on the e-pharmacy computer (401) will perform additional steps to provide for selection of the content. In particular, the content requesting software will gather data from the information entered as a part of this pharmacy transaction and encrypt in step (605) some or all of the data gathered, and possibly other information already on the e-pharmacy computer (401) such as, but not limited to, the name of the pharmacy, and transmit the encrypted information in step (607) as a first data structure to the auxiliary computer (103) over the Internet. Encryption need not be used in an alternative embodiment. However, as the information sent would generally be considered to be confidential, it is preferred that a secure encryption method be used to prevent eavesdropping. Again, the first data structure transmission is shown by the solid lines.

When the first data structure is received by the auxiliary computer (103), it will perform much the same actions as in the embodiment of FIG. 2. The auxiliary computer (103) in step (609) will confirm that the information received is without errors in transmission as is understood by those of ordinary skill in the art. If the receipt is not confirmed, the auxiliary computer (103) will request resending of the information in step (611). If the information is confirmed to be received, the auxiliary computer is step (613) will decrypt the first data structure and may then store some or all of the information therein in an associated memory or database (107) as disclosed previously.

Based on the new information provided from the first data structure, possibly in conjunction with information already in the database (107), the selection software, as in the previously discussed embodiment, in step (615) will determine whether content or information should be provided to the specific patient.

Once the auxiliary computer (103) determines in step (615) if a particular pattern or entry exists which corresponds to particular content being appropriate for distribution to the patient. The content will be selected by the auxiliary computer (103). The content again may be of any form and may include any information as discussed later.

If no content is available, the auxiliary computer (103) will generally simply do nothing. If the auxiliary computer (103) determines that content is available, the auxiliary computer (103) may provide, via the Internet, a second data structure directly to the patient computer (401) as shown in step (621). The second data structure will generally comprise the content in a form readable by the patient computer (311) (such as, but not limited to, a file formatted for Microsoft Word™, or Adobe Acrobat™ or text sent in hyper-text markup language (HTML) or in another form readable by the patient). The content may alternatively be included as part of an email, or in another form (such as, but not limited to, an instant message) which should be understandable by the patient computer (311). The patient may also be provided with a more traditional printout by mail with the medication by the e-pharmacy printing the material on a printer (not shown) and sending it with the medication. This printed content may be provided in addition to or instead of providing the content electronically. The transmission of the second data structure is shown as the dashed line in FIG. 3.

Once the patient computer (311) receives the content, the patient will generally receive notification that they have received correspondence of the type sent or the content may simply be provided to the patient, such as in a "pop-up" window. The patient may then review the content in step (623). In this embodiment, the content is not provided to the pharmacist, as the pharmacist would generally be unable to provide the content prior to sale of the prescription, which, as discussed previously, is not as desirable as having content provided before sale. Instead, the system communicates directly with the patient computer (311) so that the patient should have the content shortly after transmitting the original prescription request. In this case, the patient may have the ability to alter their order with the e-pharmacy to provide for shipment of the prescription plus anything else the patient may determine they are interested in purchasing based on the content. The direct contact also allows the patient to review the content before they obtain the medication so that they are prepared to obtain the medication. The e-pharmacy may also provide electronic shipping to the patient based on the content to further simplify their ability to purchase additional suggested products.

In the above-described embodiments, the exact form and content of the content is generally open and may include any information in any form. The information will generally be intended for consumption by the patient, but may also include information for use by the pharmacist. Therefore, the content will usually include information likely to be of use or interest to the patient and may be intended to affect the patient's behavior. In an embodiment, the content will include medication usage reminders or suggested lifestyle indications to make the medication work more effectively. In an embodiment where the prescription is new, this might include, but is not limited to, starting an exercise program, making a change in diet, or encouraging the patient to stop smoking. Further, the content may also include indicators to encourage the patient to refill the prescription promptly or to keep careful tabs on the medication as missing a day of medication while waiting for a prescription to be filled may cause unintended problems with the treatment. The embodiment of FIG. 14 includes some examples of content of this type. If consumption of the information is intended for the pharmacist, the content will generally so indicate. As the material is provided at the point of dispensing, the pharmacist is thus prepared to discuss the content with the patient when the patient comes to purchase the medication. When geared to the pharmacist, the content may include, but is not limited to, the answers to common concerns about the medication to prepare the pharmacist for questions from the patient, or may include indications of new uses for, or new risks of, the medication which the pharmacist may not be aware.

In the embodiment discussed above, the prescription is new and there may not be any need to provide for reminders or admonishments based on prior behavior of the patient with regards to the prescription. In another embodiment, such as when a prescription is being refilled, the content may include information related to the patient's extrapolated use of the medication and their possible misuse. The content can also make sure that a patient is advised of risks of misuse. For example, if a patient had gotten a prior 30-day supply of a medication, and arrived at the pharmacy 45 days after picking up their prior prescription to refill it, the content could include a notice to make sure that the patient is taking the correct dosage of their medication as it appears that the medication was not taken correctly. Further, risks from not using the medication correctly can be provided. Similar content could be provided if the patient picks up two 30 day supplies of two related medications on the same day, but when they return to refill the prescription only refills one of the two prescriptions. This admonishment could remind the patient that they need to take both medications on the same schedule for them to remain effective.

In addition to personalized information related to the patient's use of the product and other suggestions to help them to deal with the underlying condition for which the prescription was prescribed, the patient can also be supplied with commercial information. The commercial information may relate to indications for a name brand medication or may help the patient in the suggested lifestyle changes or in purchasing related products they may have need of. This may be particularly relevant if the patient filled the prescription with one brand of medication when a second brand is available, and may provide information or encouragement to switch to the second brand name medication over the first. This type of product referral is not limited to prescription medications. In an embodiment, there may also be information on other related prescription products which the patient is likely to have need of. For instance, if the patient purchased insulin, there may be information provided for diabetic test strips of a particular brand. Alternatively, information for over-the-counter (OTC) medications or supplements whose use is encouraged in conjunction with the medication (such as those related to the suggested lifestyle changes or to ease side-effects of the prescription medication) may be provided. In a yet further embodiment of the invention, the content may include information for non-medical products in which the patient may be interested. For instance, when a medication is specifically prescribed immediately following pregnancy, the content may include information on a particular brand of diapers.

While the discussion in this case relates specifically to the pharmacist dispensing the prescription being the point of contact which leads to the content being provided to the patient, the content can also or alternatively be sent to the patient directly if the patient has a device capable of accessing data from the auxiliary computer (103). To allow patient access, content may be sent directly to a patient computer (311), but will more commonly be sent to a patient access computer (301) which can be securely accessed by the patient, such as by the Internet, to provide for better indications that the content is confidentiality provided. This material may be any of the above content, or may be content which would not be relevant when the patient is in contact with the pharmacist. In an embodiment of contacting the patient directly, the auxiliary computer (103) may send the patient reminders that their current supply of medication is probably getting low and encouraging them to renew their prescription with the name brand medication and at a sponsoring pharmacy or e-pharmacy. The content may even provide simplified ordering mechanisms for such refill. Further, electronic advertising may be directly provided as part of this content. The reminders can become more regular or urgent if it is detected that the patient may not be using their medication correctly, or may not be intending to refill a specific prescription, and may encourage contacting their physician. Still further, urgent safety information, such as a product recall, can be communicated directly to the patient if it is applicable to their medications.

In an embodiment, the system can even be set up to provide reminders for the patient to be carrying out suggested lifestyle changes along with a schedule that they should be meeting for those changes, helpful information, or encouragement. For instance, if the patient is taking medications for obesity, a diet schedule may be regularly provided including suggested meal recipes that a patient could use to meet a target caloric intake for a coming week based on their prescribed medication and dose. These can be very helpful to the patient by providing more regular health reminders as well as encouragement and information to improve the likelihood of making and maintaining a lifestyle change. The user could also be directed to an online support group or similar location to help with their diet or provided with a weight monitor which can show them their success.

Such an embodiment of dialogue from the system can even be taken so far as to remind the patient to take their medication according to a complicated program. Patients with complex medication schedules who have cellular phones, pagers, or other portable communication devices capable of receiving communication from the auxiliary computer (103) or patients who have regular access to an Internet-connected computer (such as a computer at work), can receive timed reminders to take medication. The auxiliary computer (103) can send a message to the patient to take medication. The messages can be provided on a fixed schedule making it easier for the patient to remember to take their medication at prescribed times. This can be particularly beneficial to the elderly or those on very complicated medication regimens. Combined with branded information and helpful additional reminders for upcoming refills and lifestyle changes, the system can provide for a more comprehensive medication program beneficial to both the supplier of the medication and the patient.

In particular, this type of ongoing communication, allows for provision of information to the patient outside of the controlled environment of the physician's office and may occur with the patient outside the pharmacy, or in conjunction with a patient's regular pharmacy visits. The patient is provided with both peace of mind and helpful information related to their medication use. At the same time the pharmaceutical manufacturer is reassured that product information is being distributed to the correct patients in a timely manner and can gain the benefits of advertising to a highly relevant audience.

Figure 5:
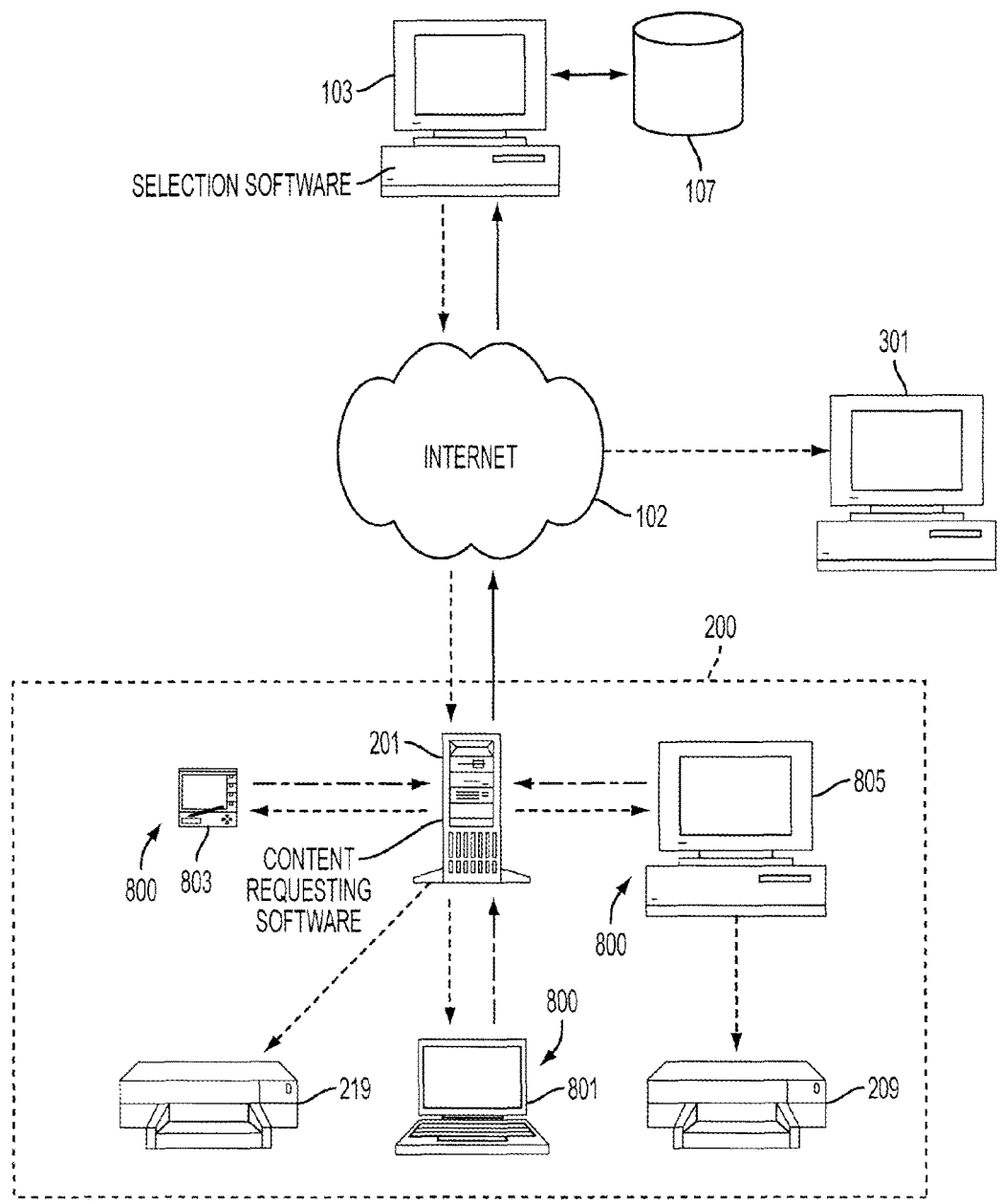
FIG. 5 Provides a block diagram of an embodiment of a patient communication system utilizing information provision in a medical provider's (physician's) office.

The above embodiments of the system provide that information is given to the patient in conjunction with the contact with the pharmacist. In the alternative embodiments depicted in FIGS. 5 through 12 and 15-16, the patient may be given the content prior to receiving the medication or going to a pharmacy to pick the medication up. In these embodiments, the content is provided around the time the medication is prescribed or at the "point of prescribing." In the embodiments of FIGS. 5 and 6 and FIGS. 15 and 16, this prior delivery occurs either at the physician's office when the prescription is first issued or renewed, or in intervening time after departing the physician's office, but before the patient has filled the initial prescription. In the embodiment of FIG. 5, the pharmacy computer (101) is not used to provide for the content selection and instead a physician's network (200) is used for the initial content selection essentially being substituted in place of the pharmacy computer (101). The physician's network (200) will generally be a system for providing computer support to the physician's office. The system may include patient scheduling, billing, clinical information, prescription services, or other functions performed at a physician's office. Alternatively, the prescription may be written out, but the physician may store the prescription information in the physician's network (200) for records purposes. With regard to content selection, the physician's server (201) will generally include content requesting software which may be integrated with other software on the physician's server (201). The physician's server (201) will generally have Internet (102) access of any form as previously discussed and will often allow Internet (102) access to any number of physician's devices (800). A physician's device (800) will generally be some form of computing device acting as a client to the physician's server (201). This may be a Handheld computer or personal digital assistant (803), a laptop computer (801), a desktop computer (805), or any other computing device used by the physician that is in communication with the physician's server (201).

Figure 6:
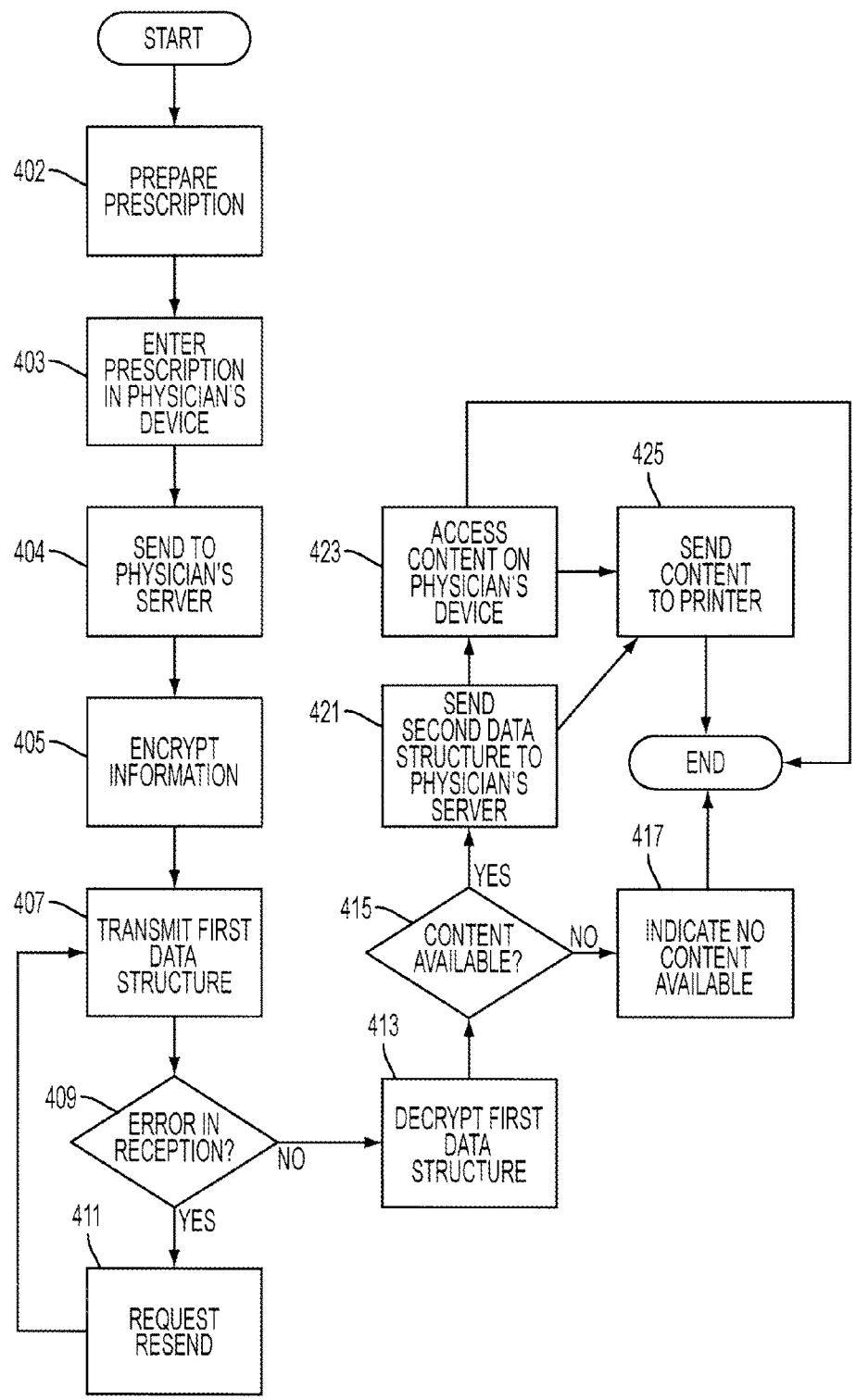
FIG. 6 Provides a flowchart of steps in an operation of the embodiment of FIG. 5.

The operation of the system of FIG. 5 preferably follows the flowchart of steps shown in FIG. 6. The physician in step (402) will prepare the prescription for the patient on the physician's device (800) after making a medical determination that such a prescription is appropriate. This may either be a new prescription, or may be additional refills for an existing prescription. To generate the prescription, or simply to record the prescription for the physician's records, the physician will enter the patient and prescription information into the physician's device (800) in step (403). This entered information may include any or all of, but is not limited to, The National Drug Code (NDC) for a prescription, the patient's age, patient's gender, patient's ID (such as a name or identifying number), patient contact information, physician identifier, prior patient behavioral data, whether the prescription is new or a refill, patient history information, or any other information of the type that may be of interest to a physician for treating the patient.

Once the information is entered, the physician's device (800) will transfer the information to content requesting software on the physician's server (201) in step (404) as indicated by the long dash short dash lines in FIG. 5. The physician's server (201) will encrypt, in step (405), some or all of the data entered, and possibly other information already on the physician's server (201) such as, but not limited to, an identification characteristic of the prescribing physician, the physician's office location, patient identifier information or other information and transmit the encrypted information in step (407) as the first data structure to the auxiliary computer (103) over the Internet. This is the solid line in FIG. 5. As in the pharmacy computer (101) transaction, encryption need not be used in an alternative embodiment.

When the first data structure is received by the auxiliary computer (103), it will be treated in a similar fashion to the previously discussed embodiments. The selection software in step (409) will confirm that the first data structure is received without errors in transmission requesting a resend in step (411) if there are errors. Once the first data structure is confirmed to be correctly received, the auxiliary computer (103) in step (413) will decrypt the information in the first data structure and may then store it in an associated memory or database (107).

Based on the new information provided from the first data structure, possibly in conjunction with information already in the database (107), the auxiliary computer (103) in step (415) will determine whether content or information should be provided to the specific patient. Again, the availability of content will generally be determined by analyzing the information and any other information already available to the auxiliary computer (103) to look for particular patterns or entries based on a predetermined set of criteria.

The selection software on the auxiliary computer (103) will determine in step (415) if a particular pattern or entry exists which corresponds to particular content being appropriate for distribution to the patient. If such content exists, the content will be selected by the auxiliary computer (103). If no content is available, the auxiliary computer (103) may send back to the physician's server (201), via the Internet, an indicator that no content is available in step (417) or the auxiliary computer (103) may simply do nothing within a prescribed time to indicate that no content is available to the physician's server (201). If the selection software determines that content is available, the auxiliary computer (103) may provide, via the Internet connection between the physician's server (201) and the auxiliary computer (103), a second data structure as shown in step (421) and indicated by the dashed line in FIG. 5. As in the embodiment of FIG. 2, the second data structure may comprise either the content in a form useable by the physician's server (201) or instructions to utilize particular content maintained in a memory cache at the physician's server (201) or a physician's device (800). The auxiliary computer (103) may also or alternatively send the second data structure directly to the patient access computer (301) as discussed elsewhere.

When the physician's server (201) receives the second data structure from the auxiliary computer (103), if the second data structure comprises actual content, the content may be sent to the associated printer (219) via the print stream for printing in step (425) or an associated physician's device (800) in step (423). If the physician's server (201) receives instructions about the content to be used, the content requesting software on the physician's server (201) may access the content in a local memory cache in step (421) and then send the content to the associated printer (219) in step (425) or a physician's device (800) in step (423). Alternatively, content on the physician's device can be accessed in step (423) if that is where the content is stored. Printing of the content will generally be of a similar form to the printing at the pharmacy printer (109).

Figure 7:
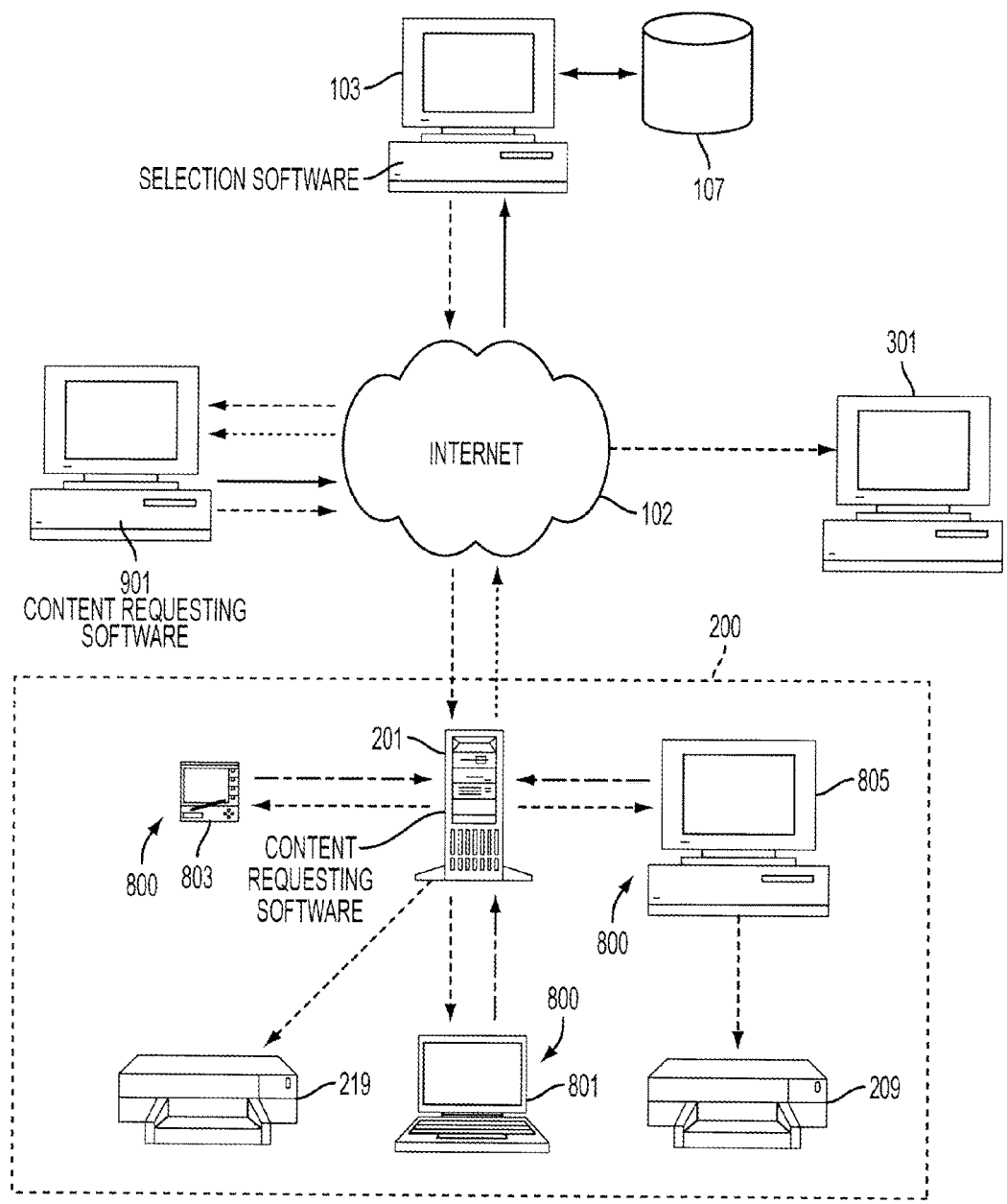
FIG. 7 Provides a block diagram of an embodiment of a patient communication system utilizing information provision from an electronic prescribing provider.
Figure 8:
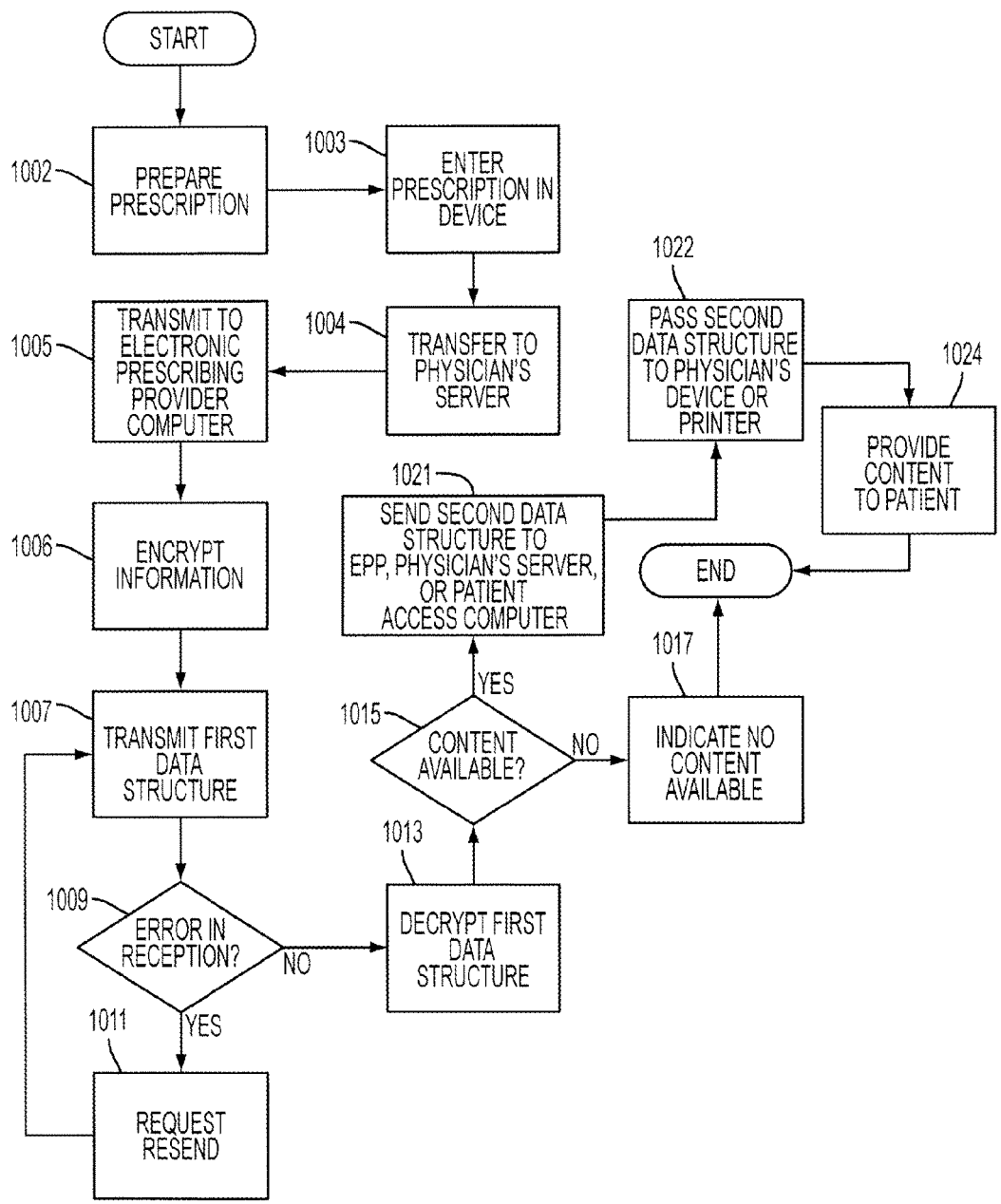
FIG. 8 Provides a flowchart of steps in an operation of the embodiment of FIG. 7
Figure 9:
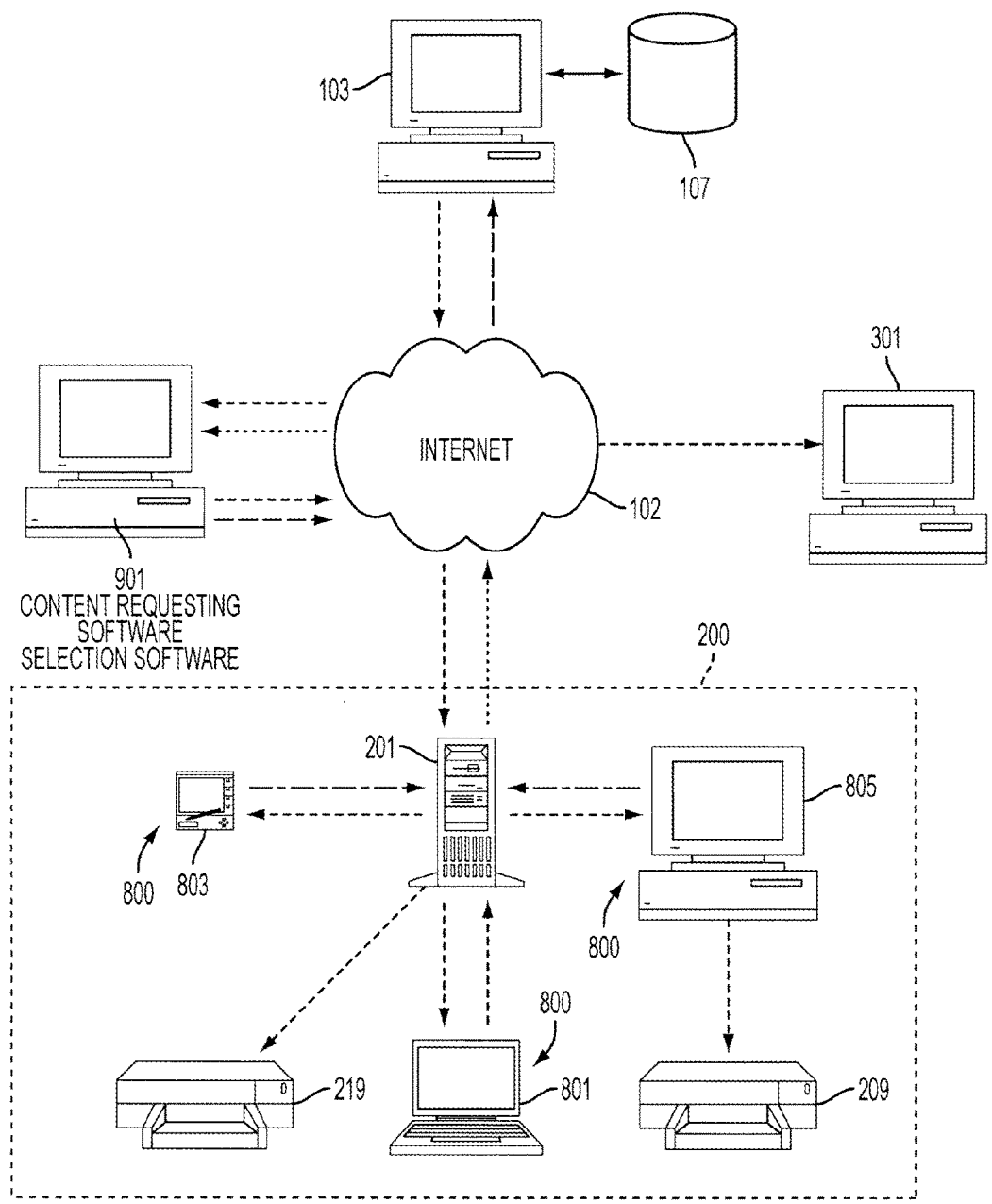
FIG. 9 Provides a block diagram of an embodiment of a patient communication system utilizing information provision from an electronic prescribing provider.
Figure 10:
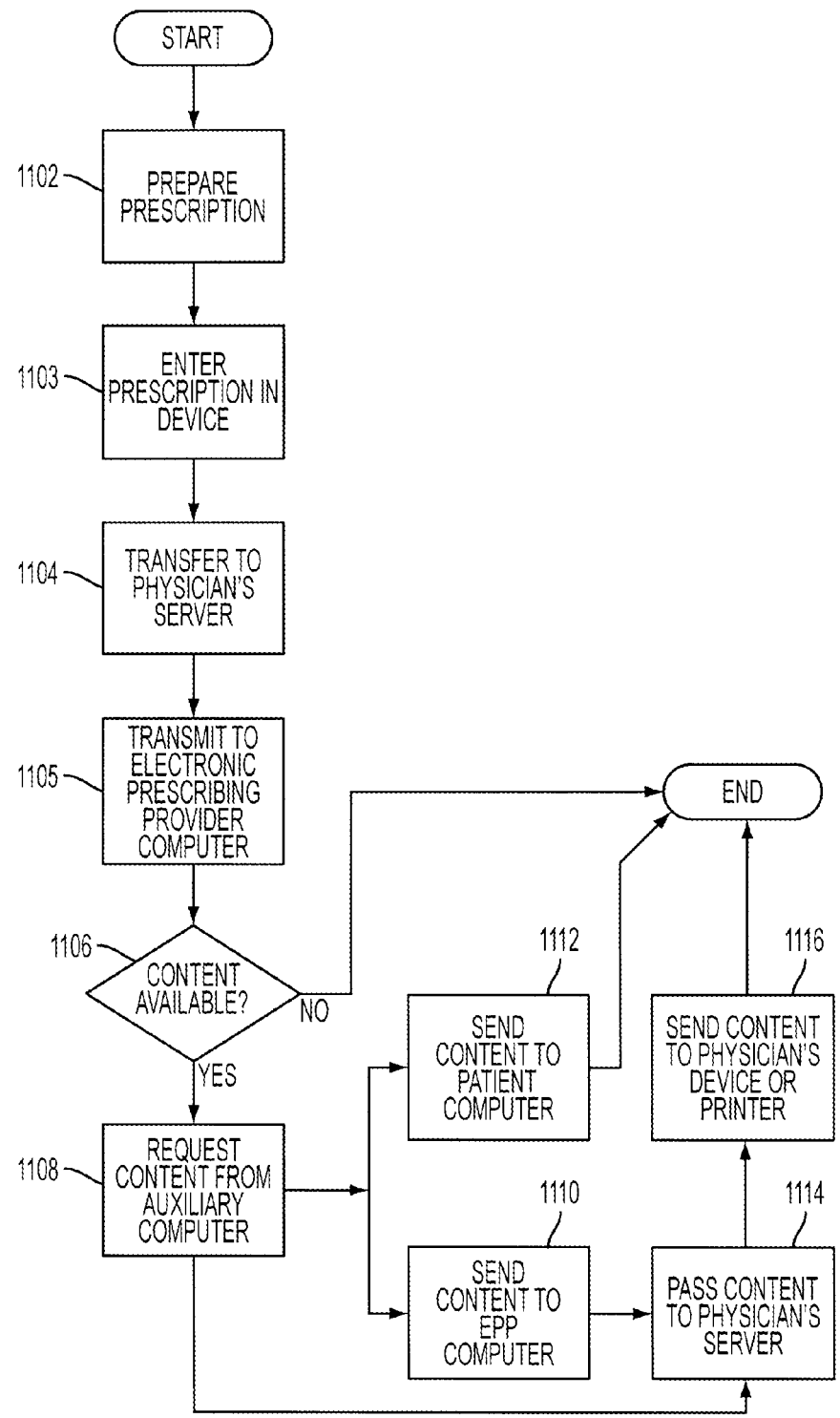
FIG. 10 Provides a flowchart of steps in an operation of the embodiment of FIG. 9
Figure 11:
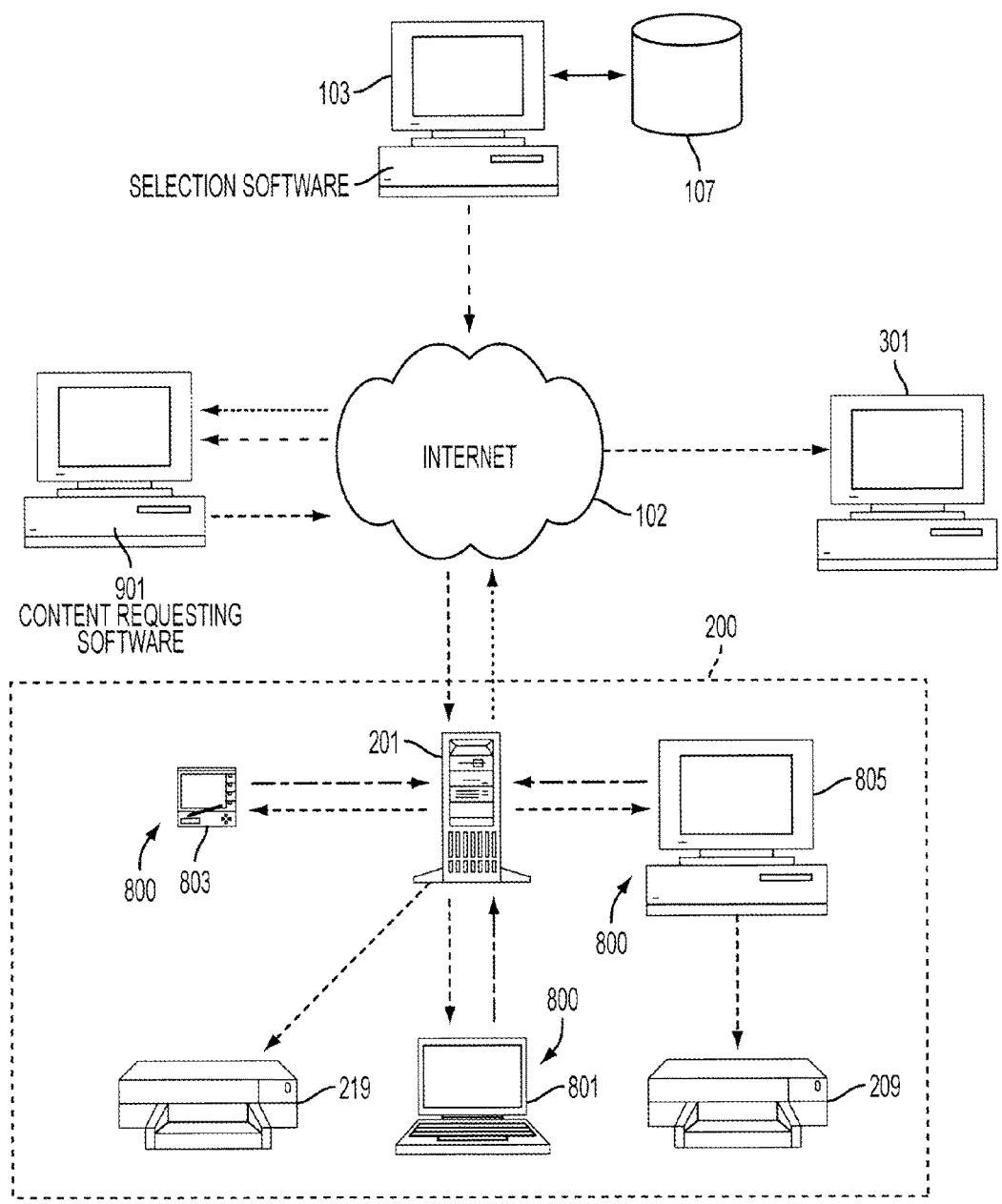
FIG. 11 Provides a block diagram of an embodiment of a patient communication system which utilizes content "push" to an electronic prescribing provider.

In another embodiment where the point of contact is the physician, the system may be arranged to utilize an electronic prescribing provider computer (901) as shown in FIGS. 7 through 12. As opposed to the e-pharmacy computer (401), electronic prescribing provider computer (901) does not generally provide medications, but instead is an aid to physicians in writing the prescriptions. FIGS. 7, 9, and 11 provide for three different embodiments of a system using an electronic prescribing provider computer (901). In these systems, the physician's device (800) is connected to the physician's server (201) forming a physician's network (200) in similar fashion to that previously discussed, which is in turn in communication with an electronic prescribing provider computer (901) generally via a network structure which may be the Internet (102). The electronic prescribing provider computer (901) will generally provide for systems and methods to assist the physician's generation of the prescription by allowing the generation of an "electronic prescription" such as by the physician entering the prescription on the physician's electronic device (800) instead of on paper. The electronic prescribing provider computer (901) then can provide the physician with the ability to print a copy of the prescription for the patient, or can fax, email, or otherwise transmit the prescription to the patient or directly to the pharmacy. The electronic prescribing provider may be a provider that only provides the services of an electronic prescribing provider, as are understood by those of ordinary skill in the art, or may provide a number of services which may include e-prescribing capability. In such a situation, the electronic prescribing provider computer (901) may provide for some or all of the functionality of the physician's server (201) discussed in conjunction with FIG. 5, may provide only specific functionality related to prescriptions, or may provide much broader functionality related to the operation of the physician's practice. The electronic prescribing provider computer (901) is therefore not limited to an e-prescriber, but may more generally provide for services to the physician. Further, an electronic prescribing computer (901) may utilize a third party pharmacy clearinghouse or other similar type of service in its operation. Such clearinghouse providing additional functionality to the electronic prescribing computer (901).

In the embodiment of FIG. 7, the system may work as shown in the flowchart of steps in FIG. 8. The physician in step (1002) will prepare the prescription for the patient after making a medical determination that such a prescription is appropriate. To generate the prescription, the physician will enter the patient and/or prescription information into the physician's device (800) in step (1003). The physician's device (800) transfers the information to the physician's server (201) in step (1004).

Once the information is entered, the physician's server (201) will transmit in step (1005) some or all of the data entered to the electronic prescribing provider computer (901) in accordance with the known operation of an electronic prescribing provider computer (901). This is shown by the dotted line in FIG. 7. Upon receipt of the information at the electronic prescribing provider computer (901), the electronic prescribing provider computer (901) will perform its usual operation to prepare and organize the electronic prescription. The content requesting software, which will generally be running on the electronic prescribing provider computer (901), will take the information received (and possibly information already available to the electronic prescribing provider computer (901)), and repackage it into the first data structure which it will send to the auxiliary computer (103) as shown by the solid line in FIG. 7. As discussed in conjunction with prior embodiments, the auxiliary computer (103) in step (1009) will confirm that the first data structure is received without errors in transmission requesting a resend in step (1011) if there is a problem. Once the first data structure is correctly received, the auxiliary computer (103) in step (1013) will decrypt the information in the first data structure and may then store it in an associated memory or database (107) as discussed previously.

Based on the new information provided from the first data structure, possibly in conjunction with information already in the database (107), the selection software on the auxiliary computer (103) in step (1015) will determine whether content or information should be provided to the specific patient. Again, the availability of content will generally be determined by analyzing the information and any other information already available to the auxiliary computer (103) to look for particular patterns or entries based on a predetermined set of criteria. If no content is available the auxiliary computer (103) will so indicate in step (1017).

If such content exists, the content will be selected by the selection software. If the selection software determines that content is available, the auxiliary computer (103) may provide in step (1021), via the Internet connection between the electronic prescribing provider computer (901), physician's server (201), and/or the auxiliary computer (103), a second data structure. As discussed in prior embodiments, the second data structure may comprise the content in a form useable by a computer or instructions to use particular content maintained in the memory cache of any of the electronic prescribing provider computer (901) the physician's server (201), or physician's device (800). The second data structure path is indicated by the various dashed lines in FIG. 7. The electronic prescribing provider computer (901) may also or alternatively receive the second data structure. If the second data structure comprises content or instructions to use content on the electronic prescribing provider computer (901), the content may be forwarded by the electronic prescribing provider computer (901) to the physician's server (201) or printer (219) which may in turn pass the content to the physician's device (800) for the physician's review or action in step (1022). The physician will generally then pass the content to the patient in step (1024). The auxiliary computer (103) and/or electronic prescribing provider computer (901) may also or alternatively transmit the content directly to the patient access computer (301) in step (1022) depending on embodiment and as discussed elsewhere.

In the embodiments of FIGS. 9 through 12 a similar operation to the embodiment of FIGS. 7 and 8 is performed, except that in these embodiments, the selection software, which in prior embodiments was discussed as being located on the auxiliary computer (103) and separate from the content requesting software, is located on the electronic prescribing provider computer (901) instead and may be combined with the content requesting software or the content. In the embodiment of FIGS. 9 and 10, the physician will generally prepare the prescription in step (1102), enter the prescription in their device (800) in step (1103) which transfers the prescription to the physician's server (201) in step (1104) and to the electronic prescribing provider computer (901) in step (1105). This is similar to the steps of the embodiment of FIG. 8. Content will generally be provided by the auxiliary computer (103). The particular piece of content is selected by the electronic prescribing provider computer (901) in step (1106) and then requested to be transmitted from the auxiliary server (103) in step (1108). This content may be sent to the electronic prescribing provider computer (901) in step (1110) to be passed to the physician's device (800), physician's server (201), or printer (219) in steps (1114) and (1116) or again may be sent directly to the patient access computer (301) in step (1112). In effect, the first data structure traveling to the auxiliary computer (103) is eliminated, and a new data structure comprising a request for particular content is sent to the auxiliary computer (103) which responds with the alternative second data structure comprising the content. In FIG. 9 these two different second data structures are indicated by the differently dashed lines.

Figure 12:
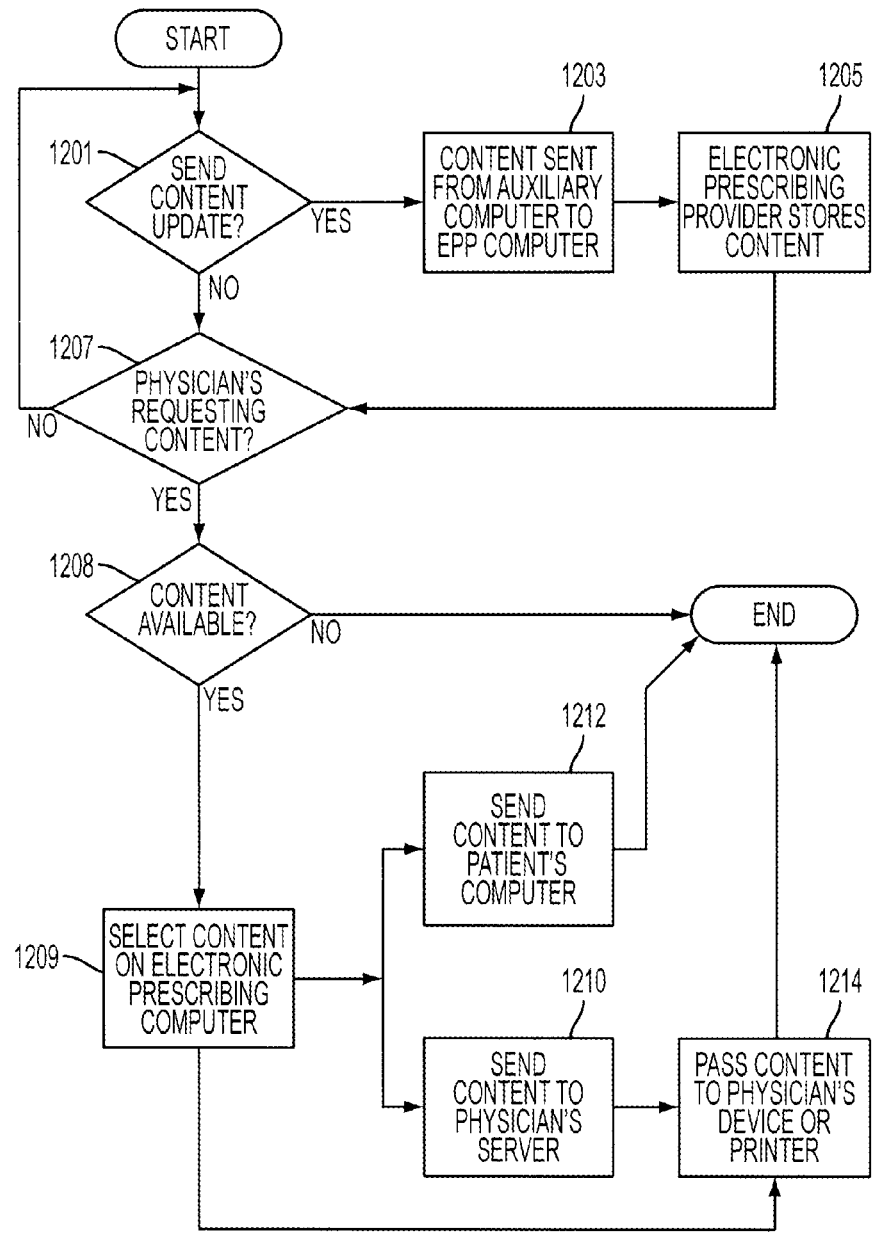
FIG. 12 Provides a flowchart of steps in an operation of FIG. 11.

The selection software being present on a machine other than the auxiliary computer (103) and possibly combined with the content requesting software is not limited to the embodiment of FIGS. 9 and 10. In FIGS. 11 and 12, the auxiliary computer operates in a software "push" configuration. In this arrangement, content is periodically sent to the electronic prescribing provider computer (901) by the auxiliary computer (103). When it is determined that a content transmission is appropriate in step (1201), the auxiliary computer (103) in step (1203) transmits content to the electronic prescribing provider computer (901). The electronic prescribing provider computer (901) then stores the content in step (1205) for later retrieval on any form of storage accessible to it. When a request for content is received in step (1207), the electronic prescribing provider computer (901) will determine if content is available in step (1208). This content will be selected by the electronic prescribing provider computer (901) in step (1204) to be passed to the physician's device (800), physician's server (201), or printer (219) in steps (1210) and (1214) or again may be sent directly to the patient access computer (301) in step (1212). In effect, the electronic prescribing provider computer (901) assumes the role of auxiliary computer (103) in selecting and storing content in this embodiment. The auxiliary computer (103) acts as a central source for content, but does not select content.

One benefit of these arrangements is that the auxiliary computer (103) can be freely updated with new content and the newest content will always be selected as the particular content on the auxiliary computer (103) at the time of the request (generally in the latest update) will be selected. Still further, this system means that the auxiliary computer (103) does not need to receive any confidential information about the patient, and no confidential information is ever transferred. Instead, the confidential information is used by existing systems which already handle confidential information to determine content, and the particular piece of content is selected without need to communicate confidential information. In a still further embodiment of this arrangement, the selection software is combined with the content requesting software forming a single software entity.

Figure 15:
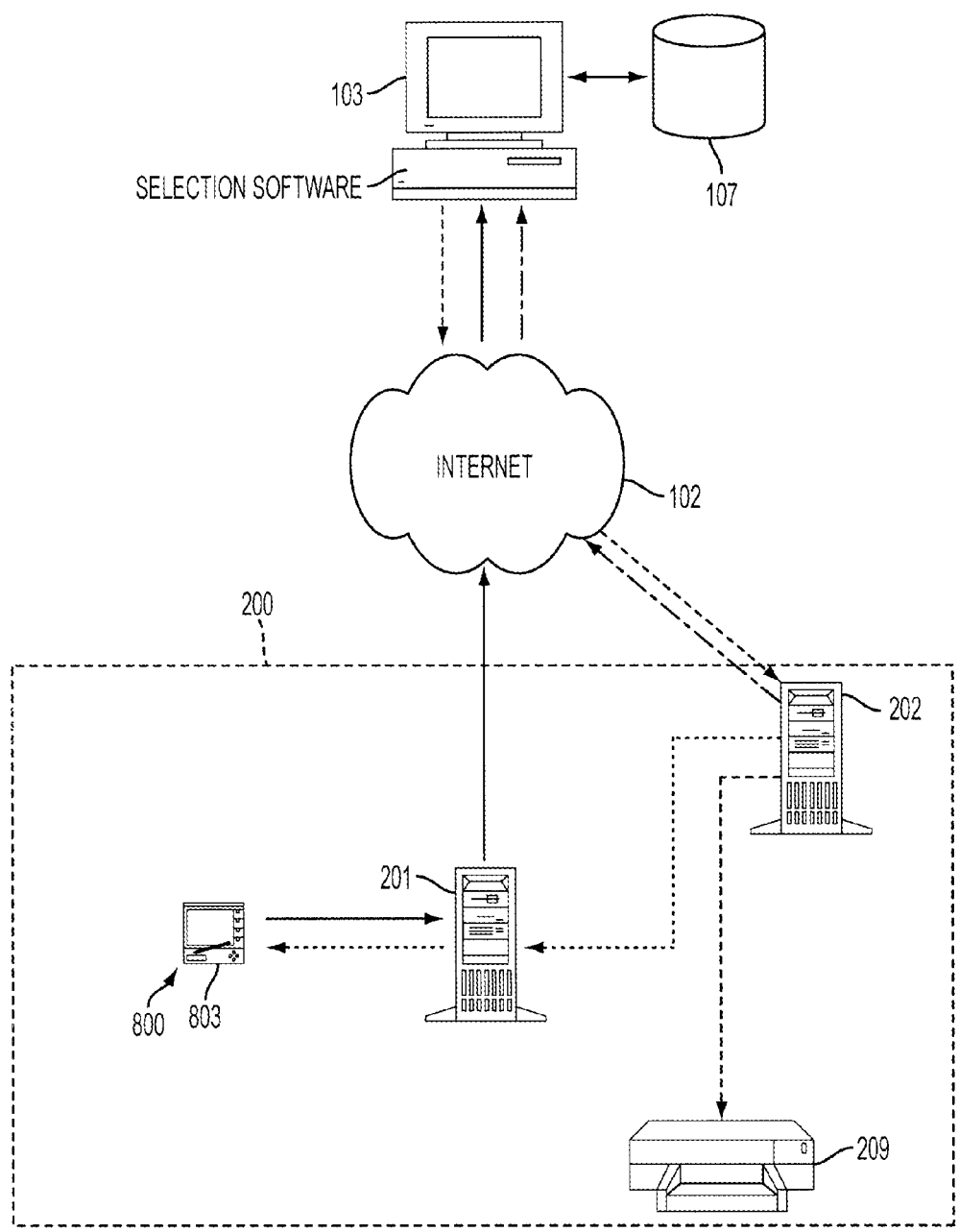

In the embodiment of FIG. 15, like in the embodiment of FIG. 5, a physician's network (200) is used for the initial content selection. However, in the embodiment of FIG. 15, the physician's server (201) will generally not be able to process the second data structure and provide for the printing of content directly. The inability to print will commonly be because the physician is using a web-based prescribing application from which printing documents is cumbersome or the content is provided in a format not generally readable, or less useable, by the physician server (201) or because the physician server (201) is not hooked to a suitable printer. Instead, content will be provided by a system termed a bridge server (202) interfacing with the physician's office printer network.

With regard to content selection, as in other embodiments the physician's server (201) will generally include content requesting software which may be integrated with other software on the physician's server (201). The physician's server (201) will again generally have Internet (102) access of any form as previously discussed and will often allow communication with any number of physician's devices (800).

In an alternative embodiment of FIG. 15, the physician's server (201) may not belong to the physician but may be an electronic prescribing vendor's server which has been provided to the physician for their use, may be accessed via a web browser at the physician's office via an application service provider (ASP) arrangement, or may be provided in other similar fashions. In such an alternative arrangement, the electronic prescribing vendor's server can assist the physician in providing electronic prescriptions and related e-prescribing services as discussed elsewhere in addition to including the content requesting software in the same fashion as discussed previously.

Figure 16:
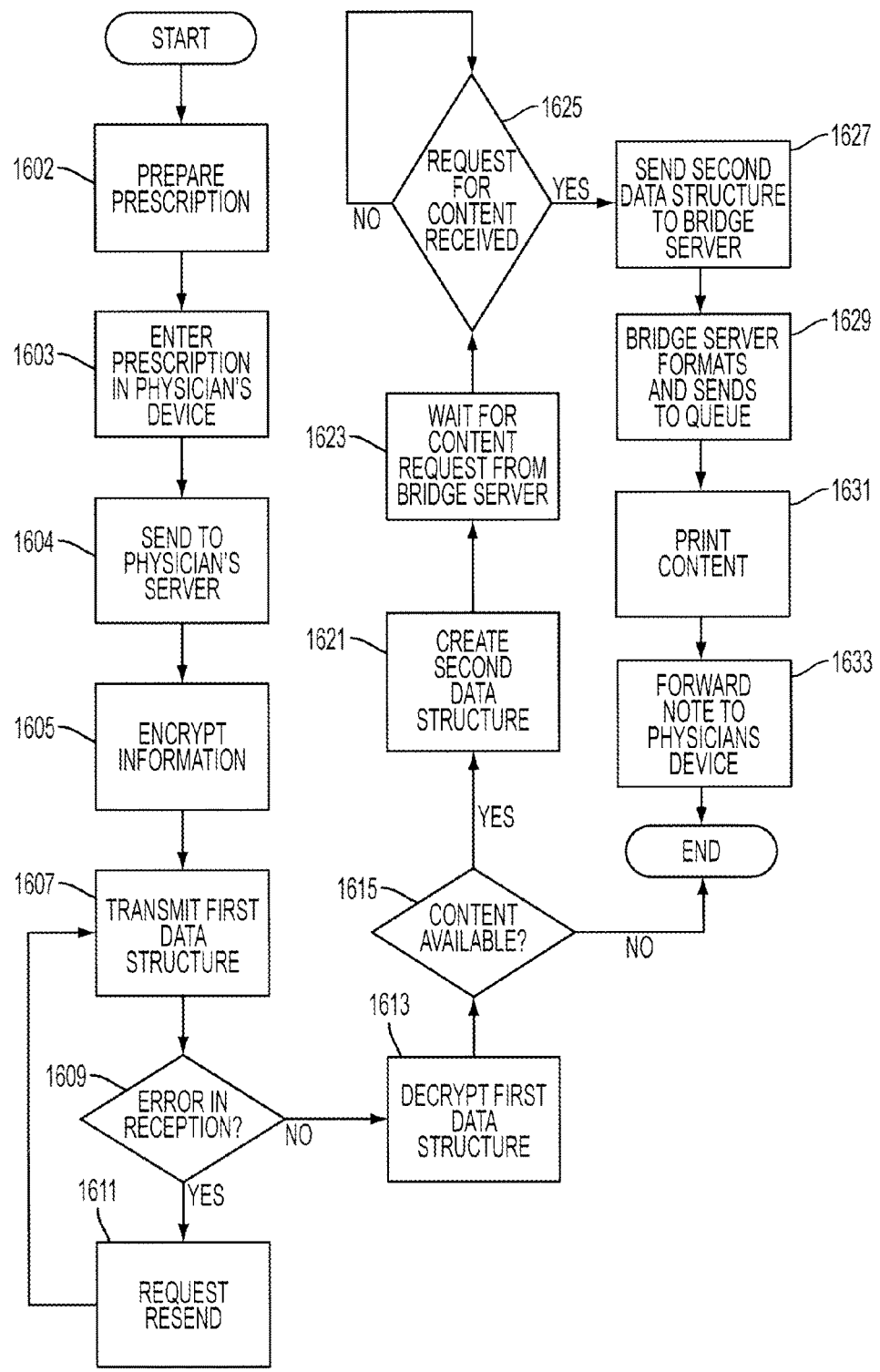
FIG. 16 provides a flowchart of steps in an operation of the embodiment of FIG. 15.

The operation of the system of FIG. 15 preferably follows the flowchart of steps shown in FIG. 16. However, as with the prior embodiments, this layout of steps is by no means limiting on the operation of the system. The physician in step (1602) will prepare the prescription for the patient on the physician's device (800) after making a medical determination that such a prescription is appropriate. This may either be a new prescription, or may be a renewal of an existing prescription. To generate the prescription, or simply to record the prescription for the physician's records, the physician will enter the patient and prescription information into the physician's device (800) in step (1603). This entered information may include any or all of, but is not limited to, The National Drug Code (NDC) for a prescription, the patient's age, patient's gender, patient's ID (such as a name or identifying number), patient contact information, physician identifier, prior patient behavioral data, whether the prescription is new or a renewal, patient history information, or any other information of the type that may be of interest to a physician for treating the patient.

Once the information is entered, the physician's device (800) will transfer the information to content requesting software on the physician's (or vendor's) server (201) in step (1604) as indicated by the solid line in FIG. 15. Alternatively, the information may have been entered directly to the physician's (or vendor's) server (201) by the physician. The physician's server (201) will encrypt, in step (1605), some or all of the data entered, and possibly other information already on the physician's server (201) such as, but not limited to, an identification characteristic of the prescribing physician, the physician's office location, patient identifier information or other information and transmit the encrypted information in step (1607) as the first data structure to the auxiliary computer (103) over the Internet. This is the solid line in FIG. 15. As in other embodiments, encryption need not be used in an alternative embodiment.

When the first data structure is received by the auxiliary computer (103), it will generally be treated in a similar fashion to the previously discussed embodiments. The selection software in step (1609) will generally confirm that the first data structure is received without errors in transmission generally requesting a resend in step (1611) if there are errors. Once the first data structure is confirmed to be correctly received, the auxiliary computer (103) in step (1613) will decrypt the information in the first data structure and may then store it in an associated memory or database (107).

Based on the new information provided from the first data structure, possibly in conjunction with information already in the database (107), the auxiliary computer (103) in step (1615) will determine whether content or information should be provided to the specific patient. Again, the availability of content will generally be determined by analyzing the information and any other information already available to the auxiliary computer (103) to look for particular patterns or entries based on a predetermined set of criteria.

The selection software on the auxiliary computer (103) will determine in step (1615) if a particular pattern or entry exists which corresponds to particular content being appropriate for distribution to the patient. If such content exists, the content will be selected by the auxiliary computer (103). If no content is available, the auxiliary computer (103) may set a flag or other indicator that no content is available in step or the auxiliary computer (103) may simply do nothing. The latter will generally be preferred as it eliminates unnecessary network traffic and provides that the bridge server (202) is not provided with unnecessary information. If the selection software determines that content is available in step (1615), the auxiliary computer (103) will create a second data structure as shown in step (1621). It will then hold this second data structure in step (1623) until it is requested. As in other embodiments, the second data structure may comprise the content, which is generally not preferred as it increases the transmitted file size and results in duplicate transmissions, or instructions to utilize particular content maintained in a memory cache at the bridge server (202).

Simultaneously to the transaction between the physician's server (201) and auxiliary computer (103) there is a bridge server (202) operating in a physical location accessible to the physician or otherwise connected to a printer (209) under the control of the physician. The bridge server (202) is set up in order to request second data structures and print content and may be designated for that sole purpose. Alternatively, the bridge server (202) may be a machine provided to the physician such as by a e-prescribing service, to allow the physician to make specialized print requests or by the owner of the auxiliary computer (107) to provide for printing capability. Regardless of its use, the bridge server (202) is capable of having content printed on a printer (209) accessible to the physician.

At regular intervals, such as every few seconds, the bridge server (202) will send a query to the auxiliary computer (103) to determine if there is any content to be printed (indicated by the dotted line in FIG. 15). This query will request from the auxiliary computer (103) any held second data structures. Further, if the bridge server (202) currently has formatted content requests queued in step (1625), it may forward them to the printer (209) in step (1629) when sending the inquiry. In the event that the auxiliary computer (103) does not have any second data structures queued, the auxiliary computer (103) will either respond with a negative indication, or simply fail to respond.

If the auxiliary computer (103) has a second data structure queued, upon such request in step (1625), the auxiliary computer (103) will generally forward the second data structure to the bridge server (202) in step (1627), which will then format the content for submission to a printer (209) and will place the print command in a print queue. The content may be stored locally on the bridge server (202), may be retrieved from an attached memory (not shown), or may have been provided by the auxiliary computer (103) in step (1629). Effectively, the bridge server (202) will act as an intermediary between the auxiliary computer (103) and the printer (209).

While the above discusses a serial transmission of content where the bridge server (202) effectively queues the content between a first time internal where it is requested from the auxiliary computer (103) and a second where it is sent to the printer (209) this is by no means necessary and the bridge server (202) may forward the content to the printer (209) upon receipt of the second data structure, at a different fixed internal, or according to any other manner.

Receipt of the content at the printer (209) will cause the content to be printed on printer (209) in step (1631). Further, it is likely that the bridge server (202) will be a computer which is generally being operated for other purposes within the physician's office or which is separate from the physician. Because of this, it is also the case that the bridge server (202) may indicate to an operator that a print job has been received and is being executed so as to trigger the operator to get the print job and deliver it by sending a message to the physician server (201) or an attached monitor or similar display device. Alternatively, the bridge server (202) may serve to provide a notice to the physician's device (800) in step (1633) indicating such receipt of a print job to notify the physician that there is content that needs to be provided to the patient. Such a notice is indicated by the dash-dot line in FIG. 15. In a still further embodiment, the actions of the bridge server (202) discussed herein may be distributed among a number of different machines which together perform the activities of the bridge server (202) as discussed herein.

These last five embodiments utilize the physician as the point of contact and help not only with providing information to the patient in conjunction with their prescription at a point when the prescription would likely be new to the patient, but also provides information to them at the point they are most likely to be receptive to it. Research has shown that people are most acutely aware of medical concerns while they are in the physician's office. They have often just discussed issues with the physician and have also just received advice and information from the physician. This advice may relate to their prescription. Therefore, providing them with the content while they are still with the physician can make them more receptive.

As in previously discussed embodiments, the content is principally intended for the patient, but may be intended for use by the physician or pharmacist to educate the patient. It is presumed that a physician prescribing a medication will have already discussed issues related to the medication with the patient in at least some fashion. In many respects, the content can memorialize the content of such discussion for easy later reference by the patient. Further, the provided content can add to what has already been expressed by the physician to make sure the information is complete.

In an embodiment, because the content is provided with the written prescription (the point of contact is the physician) and not the physical medication, the content can also be geared to helping to get the patient through their first purchase of a new medication which may be a frightening prospect. For instance, if the prescription is for a new medication, the content may provide indications of potential side effects, information on medication onset, or nearby pharmacies which should have the medication (particularly if it is after normal business hours and some pharmacies may not be open and the medication is clearly intended for immediate dispensing). Further, the content may include encouragement or information on what to expect when using the medication and that the medication regime should commence quickly. This may help to get the patient to the pharmacist and begin a medication regimen. Further, the information may encourage a patient to use a particular branded medication. Content may also relate specifically to what beginning this type of medication regimen may mean, and can again suggest to the patient lifestyle changes which they can make to make the medication more effective or to eliminate or decrease their need for it in the future. In a prescription renewal, the content can encourage a patient to stay on the medication track, recognize a patient's success, or notify the patient of a change they need to be aware of. An example of content which could be distributed by a physician in any of the embodiments of FIGS. 5 through 12 is provided in FIG. 14.

Figure 14:
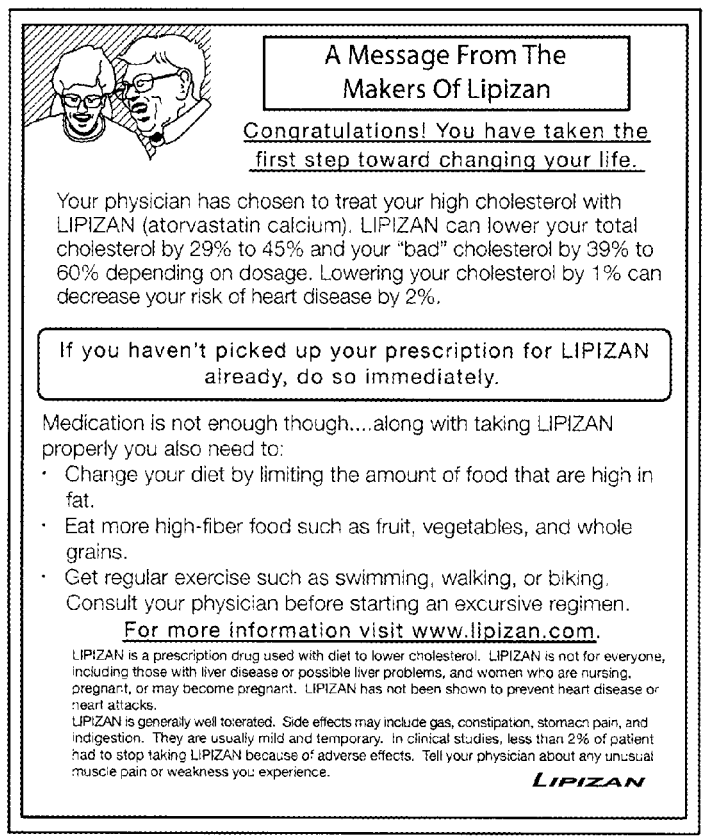
FIG. 14 Provides an embodiment of printed content which may be provided to a patient FIG. 15 Provides a block diagram of an embodiment of a patient communication system in a medical provider's (physician's) office which utilizes a queue printer.

In the embodiment of FIG. 14, an exemplary flyer of content for a fictional cholesterol medication is shown. This content includes marketing for the brand name "Lipizan" drug which has been prescribed. It also includes information encouraging the user to obtain the medication quickly. The content also indicates that lifestyle changes should be made. It should be apparent that one of the lifestyle changes (regular exercise) should not be started prior to consultation with a physician. As this content is preferably provided at the physician's office, the patient may be triggered by the content into discussing appropriate exercise regimens with their doctor prior to leaving the office.

Content may be provided for use by the physician instead of by the patient. In this case, the content may be geared to any information of interest to the physician. It may include discussion points which the physician should discuss with the patient or may include new indications (or contraindications) of the use of the medication to discuss with the patient or even to indicate to them the prescription should not be given. This may be due to recalls, drug interactions, or even concerns that the patient will abuse the medication. It could also provide for updated data with regards to drug interaction or other information which may have changed since the physician would have last prescribed the medication to insure the doctor knows of recent changes or discussions of other medications which the physician may wish to consider also prescribing to improve a patient's chance of success.

In addition, to encourage filling of the prescription and prescription provision, the content can also be used in conjunction with sample distribution of the prescribed medication. While medication samples are a popular and effective method for providing quick relief to many individuals which may not be able to fill a prescription right away or may need only a limited supply, they are often problematic as there is often no fixed literature distribution with a sample. When prescribing a medication or simply when providing a limited sample, the first data structure may include indications that samples were provided (and how many). In this case, the physician takes on part of the role of the pharmacist. The content provided in this situation may be specifically geared to making sure that the patient understands the samples they have received and how to use them as well as how to get the associated prescription filled if one is provided.

This type of patient contact is further useful if the prescription is not filled shortly after it is made. If the physician provides a 5-day sample, and after 6 days the prescription has not been filled, the patient may receive content indicating they should contact their physician as they may not be taking the medication correctly or remind them to fill the prescription. This system further provides for improved control for potentially dangerous medication samples being used for illicit purposes. Further, it provides for physician follow up in case there is a misunderstanding related to the medication.

Figure 13:
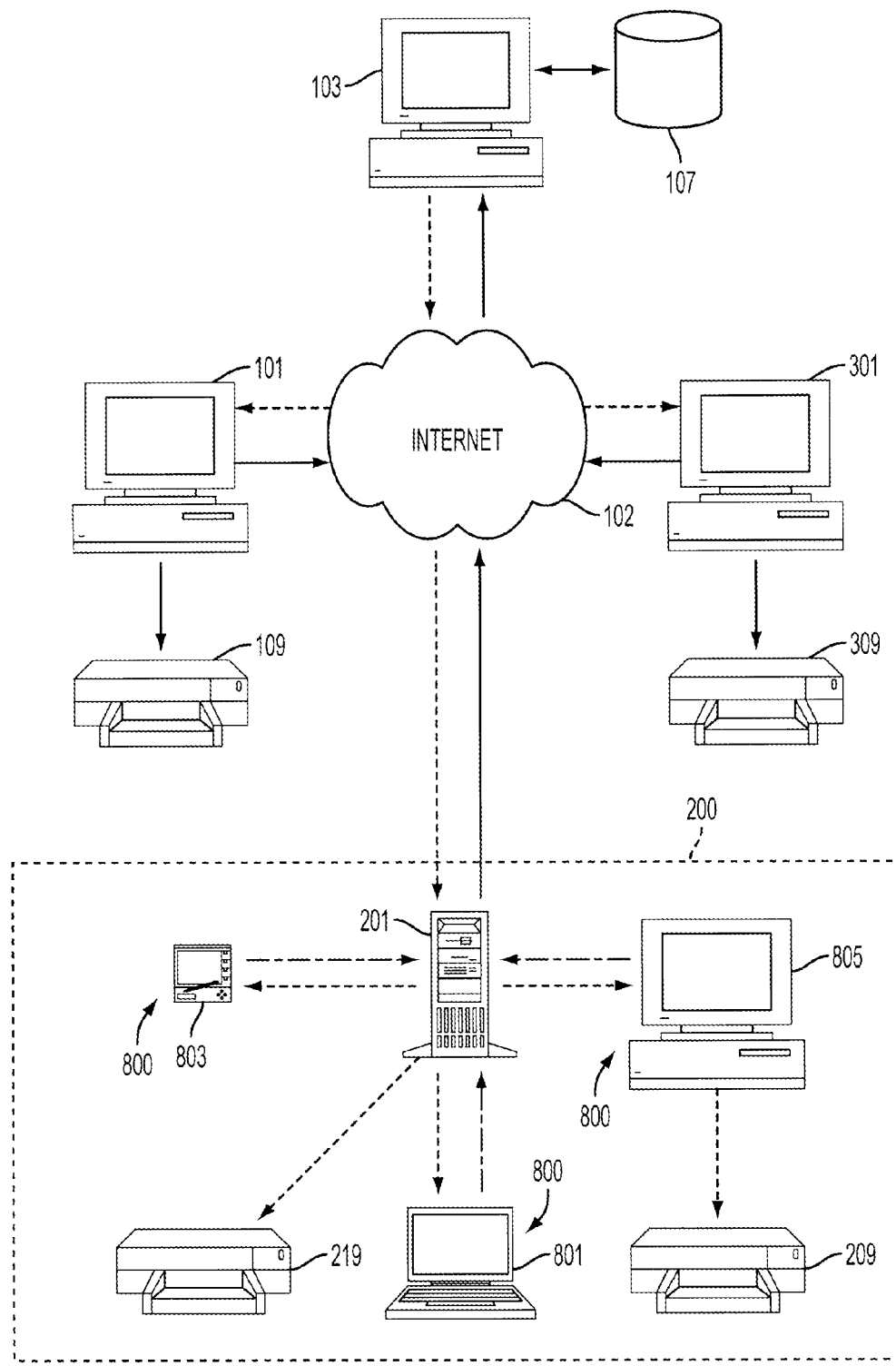
FIG. 13 Provides a block diagram of an embodiment of the invention for ongoing direct dialogue with the patient.

In another embodiment of the invention, contact as discussed previously is combined. In the above-described embodiments of FIGS. 1 through 12, the patient only received content at one of the pharmacy or the physician. In the embodiment of FIG. 13 the systems of the prior embodiments may be combined into an integrated communication system whereby the pharmacy computer (101), physician's computer (201) and patient access computer (301) are all interlinked via the Internet to the auxiliary computer (103). In this embodiment, the patient may be provided with information when they initially receive their prescription according to the embodiment of FIG. 6. This information may then be integrated with information when they pick up and refill the prescription at the pharmacy computer (101) or at the patient access computer (301) before, during, or after those communications.

While the embodiment of FIG. 13 shows only a single pharmacy computer (101) and a single physician's server (201), multiple of these machines may be interconnected to the single auxiliary computer system (103). An electronic prescribing provider computer (901) may also be included based on the embodiment of FIGS. 8-12. In this type of system, a steady dialogue can be maintained between the patient and the auxiliary computer (103). Further, the system can recognize that some changes may be indicative of a need to update information. For instance, if the patient suddenly fills two prescriptions in a different state, the system may be able to ask if the patient has recently moved. Further, such an integrated system can provide notice of when a prescription may be being abused because the same prescription is being duplicatively filled in multiple locations. Further, while the embodiment of FIG. 13 presumes direct contact between the pharmacy computer (101), physician computer (201), and auxiliary computer (103), any of the arrangements of the other embodiments could be used in an alternative embodiment.

As should be clear from the above discussed embodiments of the system, the content provided will depend on the particular embodiment of the system. In an embodiment, the content will be provided commercially as part of a paid activity by the medication provider. In particular, the content will include commercial information and may relate to the prescription medication being purchased (such as for products for use with the prescription), other medications or products (whether prescription, OTC, or any other products) that a particular patient might be interested in based on the prescription medication being purchased, or any other type of advertising for products and services. The embodiment of FIG. 14 includes commercial content as well as other content which might be provided in a physician's office. This commercial information can both provide for advertising to the patient and can encourage a patient to select one branded medication over another. This can help the medication manufacturer to improve sales. As such, a system is valuable to the medication supplier. The auxiliary computer (103) may therefore be able to operate by payment for supplying commercial information in conjunction with non-commercial information.

In an embodiment of the invention, the content can also provide for an error checking function related to the distribution of medication. In particular, the second data structure will generally not include confidential information of the patient. The auxiliary system will generally not provide as part of the second data structure any confidential information. In this way, the system cannot be abused by calling up or providing records that a patient has not been given access to. The system, however, will select content it is believed appropriate to the patient. If this content is illogical to the patient, the patient may contact the physician or pharmacy to insure that the prescription was correct. In this way, the patient may recognize a mistake without the mistake revealing another's confidential information.

For instance, if content was provided discussing the decreased dosage of medication being prescribed, the patient may question their physician if such decreased dosage is correct if they were not expecting the dosage to be decreased. Further, if content discussed treatment or lifestyle changes for conditions that the patient does not have, the patient may double check with the pharmacy or physician that the prescribed medication is correct. Further, if the patient received reminders to renew a prescription before they ran out of pills, they may check with their physician if the medication is being taken correctly or with the pharmacy to determine if the medication was dispensed in the correct amount. While this error checking function is not exact, it is one more path of dialogue to help the patient with their medications.

Further, while the above described embodiments relate specifically to an auxiliary computer (103), pharmacy computer (101), physician's computer (201), patient access computer (301) e-pharmacy computer (401), and electronic prescribing provider's computer (901) sending information via the Internet using packetized or other transfer of data, it should be recognized that communication technology is changing quickly and other embodiments may utilize alternative data transmission structures, protocols, and networks for transmission as they become available. Further, in another embodiment, the auxiliary computer (103) may provide notice to a human working with the auxiliary computer (103) to contact the patient. This may occur via mail, voice transmission, or any other form of communication. This may be particularly desirable where there are concerns for a patient's potential misunderstanding of a prescription medication, or urgent safety messages.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A method for generating information at a physician's office for a patient related to a prescribed medication, the method comprising:
    providing:
        a physician's server attached to the Internet and running content requesting software;
        an auxiliary computer attached to the Internet and running selection software;
        a bridge server; and
        a printer connected to said bridge server and located at said physician's office;
    entering prescription information into said content requesting software, as part of a medication being prescribed to a patient;
    said content requesting software forming a first data structure including at least a portion of said prescription information;
    said content requesting software transmitting said first data structure from said physician's server to said auxiliary computer;
    said selection software using at least a portion of said first data structure to select content for said patient;
    said bridge server requesting a communication from said auxiliary computer;
    only upon receipt of such a request from said bridge server, said auxiliary computer sending a second data structure indicative of said content to said bridge server;
    said bridge server sending said content to said printer;
    said printer printing said content at said physician's office.

2. The method of claim 1 wherein said second data structure comprises said content.

3. The method of claim 1 wherein said second data structure references content on said bridge server.

4. The method of claim 1 wherein said bridge server reformats said content into material understood by said printer.

5. The method of claim 1 wherein said content functions to induce said patient to purchase a particular product.

6. The method of claim 5 wherein said content functions to induce said patient to purchase a particular brand of medication.

7. The method of claim 1 wherein said entering occurs on a physician's device in communication with said physician's server.

8. The method of claim 7 wherein said physician's device comprises a handheld computer.

9. The method of claim 7 wherein said physician's device indicates when said content is printed.

10. The method of claim 1 wherein said physician's server comprises an electronic prescribing vendor's server.

11. The method of claim 1 wherein said physician's server comprises a web browser accessing an electronic prescribing vendor's server acting as an application service provider (ASP).

12. The method of claim 1 wherein said bridge server queues said content.

13. The method of claim 7 wherein physician's server is remote from said physician's office.

14. The method of claim 13 wherein said bridge server is remote from said physician's office.

15. The method of claim 1 wherein said bridge server is remote from said physician's office.

* * * * *